United States Patent
Ramachandra et al.

(10) Patent No.: US 12,268,670 B2
(45) Date of Patent: *Apr. 8, 2025

(54) COMBINATION OF SMALL MOLECULE CD-47 INHIBITORS WITH OTHER ANTI-CANCER AGENTS

(71) Applicant: Aurigene Oncology Limited, Karnataka (IN)

(72) Inventors: Muralidhara Ramachandra, Bangalore (IN); Pottayil Govindan Nair Sasikumar, Bangalore (IN); Girish Chandrappa Daginakatte, Bangalore (IN); Kiran Aithal Balkudru, Bangalore (IN)

(73) Assignee: AURIGENE ONCOLOGY LIMITED, Karnataka (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,325

(22) Filed: Apr. 25, 2022

(65) Prior Publication Data

US 2022/0241248 A1     Aug. 4, 2022

Related U.S. Application Data

(63) Continuation of application No. 16/678,594, filed on Nov. 8, 2019, now Pat. No. 11,311,517.

(30) Foreign Application Priority Data

Nov. 8, 2018 (IN) .............................. 201841042108

(51) Int. Cl.
*A61K 31/4245* (2006.01)
*A61P 35/00* (2006.01)
*A61K 45/06* (2006.01)
*C07K 16/28* (2006.01)

(52) U.S. Cl.
CPC .......... *A61K 31/4245* (2013.01); *A61P 35/00* (2018.01); *A61K 45/06* (2013.01); *C07K 16/2887* (2013.01)

(58) Field of Classification Search
CPC .................................................. A61K 31/4245
USPC .......................................................... 514/364
See application file for complete search history.

(56) References Cited

U.S. PATENT DOCUMENTS

2016/0304609 A1   10/2016   Liu et al.
2017/0081407 A1   3/2017    Grosveld et al.

FOREIGN PATENT DOCUMENTS

| WO | 2015033299 A1 | 3/2015 |
| WO | 2016/142833 A1 | 9/2016 |
| WO | 2016142886 A1 | 9/2016 |
| WO | 2016188449 A1 | 12/2016 |
| WO | 2017194627 A1 | 11/2017 |
| WO | 2017194634 A1 | 11/2017 |
| WO | 2018/047139 A1 | 3/2018 |
| WO | 2018073754 A1 | 4/2018 |
| WO | 2019138367 A1 | 7/2019 |
| WO | 2019175799 A2 | 9/2019 |

OTHER PUBLICATIONS

Berg, et al., Pharmaceutical Salts, Journal of Pharmaceutical Sciences (1977) vol. 66, Issue 1, p. 1-19.
Mark. P. Chao, et al,The CD47-SIRPa pathway in cancer immune evasion and potential therapeutic implications, Current Opinion in Immunology (2012) vol. 24, Issue 2, p. 225-232.
Qiangguo Gao, et al., Blockade of CD47 ameliorates autoimmune inflammation in CNS by suppressing IL-1-triggered infiltration of pathogenic Th17 cells, Journal of Autoimmunity (2016) vol. 69, p. 74-85.
Yoko Kojima et al., CD47-blocking antibodies restore phagocytosis and prevent atherosclerosis, Nature (2016) vol. 536, Issue 7614, p. 86-90.
International Preliminary Report on Patentability issued May 11, 2021 in Int'l Application No. PCT/182019/059602.

*Primary Examiner* — Taofiq A Solola
(74) *Attorney, Agent, or Firm* — MEDLER FERRO WOODHOUSE & MILLS PLLC

(57) ABSTRACT

The present invention relates to a composition of a CD47-SIRPα blocking agent and one or more anti-cancer agent(s), where the CD47-SIRPα blocking agents are represented by a compound of formula (I). The present invention also relates to a method of treating a cancer in a subject by administering a therapeutically effective amount of a CD47-SIRPα blocking agent represented by formula (I) in combination with one or more anti-cancer agent(s).

21 Claims, 2 Drawing Sheets

COMBINATION OF SMALL MOLECULE CD-47 INHIBITORS WITH OTHER ANTI-CANCER AGENTS

CROSS-REFERENCE TO RELATED APPLICATIONS

This non-provisional application is a continuation of U.S. application Ser. No. 16/678,594 filed Nov. 8, 2019, now U.S. Pat. No. 11,311,517, which claims benefit under 35 U.S.C. § 1.119(a) of Indian provisional application number 201841042108, filed on Nov. 8, 2018, the contents of which are hereby incorporated by reference in its entirety.

TECHNICAL FIELD

The present invention relates to a pharmaceutical composition comprising small molecule CD-47-SIRPα pathway inhibitors and one or more agents capable of stimulating receptors such as activating Fc-receptors (FcRs) or other prophagocytic receptors.

BACKGROUND

The CD47/SIRPα axis is established as a critical regulator of myeloid cell activation and serves as an immune checkpoint for macrophage mediated phagocytosis. Because of its frequent upregulation in several cancers, CD47 contributes to immune evasion and cancer progression. CD47 regulates phagocytosis primarily through interactions with SIRP1α expressed on macrophages. Blockade of SIRP1α/CD47 has been shown to dramatically enhance tumor cell phagocytosis and dendritic cells maturation for better antigen presentation leading to substantially improved antitumor responses in preclinical models of cancer (M. P. Chao et al. Curr Opin Immunol. 2012 (2): 225-232). Disruption of CD47-SIRPα interaction is now being evaluated as a therapeutic strategy for cancer with the use of monoclonal antibodies targeting CD47 or SIRPα and engineered receptor decoys.

CD47 is expressed on virtually all non-malignant cells, and blocking the CD47 or the loss of CD47 expression or changes in membrane distribution can serve as markers of aged or damaged cells, particularly on red blood cells (RBC). Alternatively, blocking SIRPα also allows engulfment of targets that are not normally phagocytosed, for those cells where pre-phagocytic signals are also present. CD47 is a broadly expressed transmembrane glycoprotein with a single Ig-like domain and five membrane-spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells.

CD47 is also constitutively upregulated on a number of cancers such as Non-Hodgkin Lymphoma (NHL), Acute myeloid leukemia (AML), breast, colon, glioblastoma, glioma, ovarian, bladder and prostate cancers, etc. Overexpression of CD47 by tumor cells, which efficiently helps them to escape immune surveillance and killing by innate immune cells. However, in most of the tumor types, blockade of the CD47-SIRPα interaction as a single agent may not be capable of inducing significant phagocytosis and antitumor immunity, necessitating the need to combine with other therapeutic agents. The concomitant engagement of activating receptors such as Fc-receptors (FcRs) or other prophagocytic receptors (collectively known as "eat-me" signals) may be necessary for exploiting the maximum potential of the CD-47-SIPRα pathway blockade.

The role of engagement of prophagocytic receptors is proved by inefficiency to trigger phagocytosis either by anti-CD47 F(ab) fragments, single chain variable fragments of CD-47 or non-Fc portion-containing SIRPα proteins in blocking of the CD47-SIRPα interaction. When activating prophagocytic receptors are engaged, as evident in the case of using Fc portion-containing blocking anti-CD47 antibodies, CD47-SIRPα blockade is able to trigger more efficient phagocytosis. Combining CD47-SIRPα blocking agents with therapeutic antibodies (Fc-containing) targeting tumor antigens stimulate activating Fc receptors (FcRs) leading to efficient phagocytosis. The Fc portion of therapeutic antibody targeting tumor antigen also induces antibody-dependent cellular cytotoxicity (ADCC), which also adds to the therapeutic efficacy. Hence antibodies selected from the group consisting of rituximab, herceptin, trastuzumab, alemtuzumab, bevacizumab, cetuximab and panitumumab, daratumumab due to its tumor targeting nature and ADCC, can trigger more efficient phagocytosis.

Earlier approaches to disrupt CD47-SIRPα interaction utilized monoclonal antibodies targeting CD47 or SIRPα and engineered receptor decoys fused to Fc fragment. However, a concern with this approach is that CD47 is highly expressed on both hematopoietic and non-hematopoietic normal cells. Hence along with tumor cells CD47-SIRPα blocking agents containing Fc-portion may also target many normal cells potentially leading to their elimination by macrophages. The interaction of blocking antibodies with normal cells is considered as a major safety issue resulting in anemia, thrombocytopenia, and leukopenia. These agents may also affect solid tissues rich in macrophages such as liver, lung, and brain. Hence it may be ideal to block the CD47-SIRPα interaction by agents devoid of Fc portion, such as small molecules, peptides, Fab fragments etc. while activating prophagocytic receptors in tumor cells by appropriate combinations to induce efficient phagocytosis of tumor cells.

Apart from Fc Receptors, a number of other prophagocytic receptors are also reported to promote engulfment of tumor cells in response to CD47-SIRPα blockade by triggering the phagocytosis. These include receptors for SLAMF7, Mac-1, calreticulin and possibly yet to identified receptors. B cell tumor lines such as Raji and other diffuse large B cell lymphoma express SLAMF7 and are implicated in triggering prophagocytic signals during CD47-SIRPα blockade.

Therapeutic agents known to activate prophagocytic receptors are also therefore ideal partners for use in combination with CD47-SIRPα blocking agents to achieve efficient phagocytosis. These agents include proteasome inhibitors (bortezomib, ixazomib and carfilzomib), Anthracyclines (Doxorubicin, Epirubicin, Daunorubicin, Idarubicin, Mitoxantrone) Oxaliplatin, Cyclophosphamide, Bleomycin, Vorinostat, Paclitaxel, 5-Fluorouracil, Cytarabine, BRAF inhibitory drugs (Dabrafenib, Vemurafenib), PI3K inhibitor, Docetaxel, Mitomycin C, Sorafenib, Tamoxifen and oncolytic viruses.

Apart from the specific agents known to have effect on 'eat me' signals other agents including Abiraterone acetate, Afatinib, Aldesleukin, Aldesleukin, Alemtuzumab, Anastrozole, Axitinib, Belinostat, Bendamustine, Bicalutamide, Blinatumomab, Bosutinib, Brentuximab, Busulfan, Cabazitaxel, Capecitabine, Carboplatin, Carfilzomib, Carmustine, Ceritinib, Clofarabine, Crizotinib, Dacarbazine, Dactinomycin, Dasatinib, Degarelix, Denileukin, Denosumab, Enzalutamide, Eribulin, Erlotinib, Everolimus, Exemestane, Exemestane, Fludarabine, Fulvestrant, Gefitinib, Goserelin, Ibritumomab, Imatinib, Ipilimumab, Irinotecan, Ixabepilone, Lapatinib, Lenalidomide, Letrozole, Leucovorin, Leuprolide, Lomustine, Mechlorethamine, Megestrol, Nelarabine, Nilotinib, Nivolumab, Olaparib, Omacetaxine, Palbociclib, Pamidronate, Panitumumab, Panobinostat, Pazopanib, Pegaspargase, Pembrolizumab, Pemetrexed Disodium, Pertuzumab, Plerixafor, Pomalidomide, Ponatinib, Pralatrexate, Procarbazine, Radium 223, Ramucirumab, Regorafenib, rIFNa-2b, Romidepsin, Sunitinib, Temozolomide, Temsirolimus, Thiotepa, Tositumomab, Trametinib, Vinorelbine, Methotrexate, Ibrutinib, Aflibercept, Toremifene, Vinblastine, Vincristine, Idelalisib, Mercaptopurine and Thalidomide could potentially have effect on 'eat me' signal pathway on combining with CD-47-SIRPα blocking agents.

In addition to the therapeutic agents mentioned above, other treatment modalities that are in use in cancer therapy also activate prophagocytic receptors, and thus can be combined with CD47-SIRPα blocking agents to achieve efficient phagocytosis. These include Hypericin-based photodynamic therapy (Hyp-PDT), radiotherapy, High-hydrostatic pressure, Photofrin-based PDT and Rose Bengal acetate-based PDT.

However, there is an unmet need for combining small molecule CD-47-SIRPα pathway inhibitors with agents capable of stimulating activating receptors such as Fc-receptors (FcRs) or other prophagocytic receptors, or combining with other treatment modalities that are in use in cancer therapy to activate prophagocytic receptors for exploiting the maximum potential of the CD-47-SIRPα pathway blockade.

SUMMARY OF INVENTION

The present invention provides a composition comprising small molecule CD-47-SIRPα pathway inhibitors with agents that stimulate activating receptors such as Fc-receptors (FcRs) or other prophagocytic receptors, or combining with other treatment modalities that are in use in cancer therapy to activate prophagocytic receptors for exploiting the maximum potential of the CD-47-SIRPα pathway blockade.

In one aspect of the invention, provided herein, is a composition comprising a CD47-SIRPα blocking agent and one or more anti-cancer agent(s) wherein the CD-47-SIRPα blocking agent is a small molecule represented by a compound of formula (I):

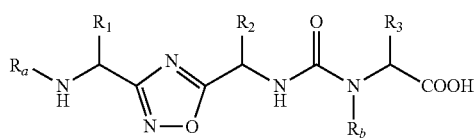

or a pharmaceutically acceptable salt or an amide or an ester, or a stereoisomer thereof; wherein, $R_a$ is hydrogen; and $R_1$ represents hydrogen, —(CH$_2$)$_2$CONH$_2$, —(CH$_2$)$_2$COOH, —(CH$_2$)$_3$NHC(=NH)NH$_2$, —(CH$_2$)$_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring;

$R_2$ represents hydrogen, —(CH$_2$)$_3$NHC(=NH)NH$_2$, —(CH$_2$)$_2$CONH$_2$, —(CH$_2$)$_2$COOH, —CH$_2$-aryl, or —CH$_2$-heteroaryl, $R_b$ is hydrogen; and $R_3$ represents hydrogen, —CH$_2$-aryl, —(CH$_2$)$_3$NHC(=NH)NH$_2$, —(CH$_2$)$_2$CONH$_2$, —(CH$_2$)$_2$COOH, —(CH$_2$)$_4$NH$_2$ or —CH$_2$-heteroaryl, or $R_b$ and $R_3$, together with the atoms to which they are attached form a pyrrolidine ring.

In another aspect, the present invention relates to a method for treating a subject presenting a dysregulated CD47 pathway, comprising administering to the subject in need thereof a therapeutically effective amount of compound of formula (I), or a pharmaceutically acceptable salt or an amide or an ester, or a stereoisomer thereof in combination with one or more anti-cancer agent(s).

Yet another aspect of the present invention provides a method of treating diseases or disorders mediated by CD47 which comprises administering a compound of formula (I) or a pharmaceutically acceptable salt or an amide or an ester, or a stereoisomer thereof in combination with one or more anti-cancer agent(s).

In a further aspect of the invention, provided herein, a combination comprising CD47-SIRPα blocking agent and one or more anti-cancer agent(s) wherein the small molecule CD-47-SIRPα blocking agent is represented by a compound of formula (I):

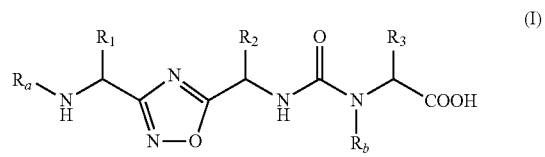

or a pharmaceutically acceptable salt or an amide or an ester, or a stereoisomer thereof; wherein, $R_a$ is hydrogen; and $R_1$ represents hydrogen, —(CH$_2$)$_2$CONH$_2$, —(CH$_2$)$_2$COOH, —(CH$_2$)$_3$NHC(=NH)NH$_2$, —(CH$_2$)$_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring;

$R_2$ represents hydrogen, —(CH$_2$)$_3$NHC(=NH)NH$_2$, —(CH$_2$)$_2$CONH$_2$, —(CH$_2$)$_2$COOH, —CH$_2$-aryl, or —CH$_2$-heteroaryl, $R_b$ is hydrogen; and $R_3$ represents hydrogen, —CH$_2$-aryl, —(CH$_2$)$_3$NHC(=NH)NH$_2$, —(CH$_2$)$_2$CONH$_2$, —(CH$_2$)$_2$COOH, —(CH$_2$)$_4$NH$_2$ or —CH$_2$-heteroaryl, or $R_b$ and $R_3$, together with the atoms to which they are attached form a pyrrolidine ring.

DETAILED DESCRIPTION OF THE INVENTION

Figure 1:
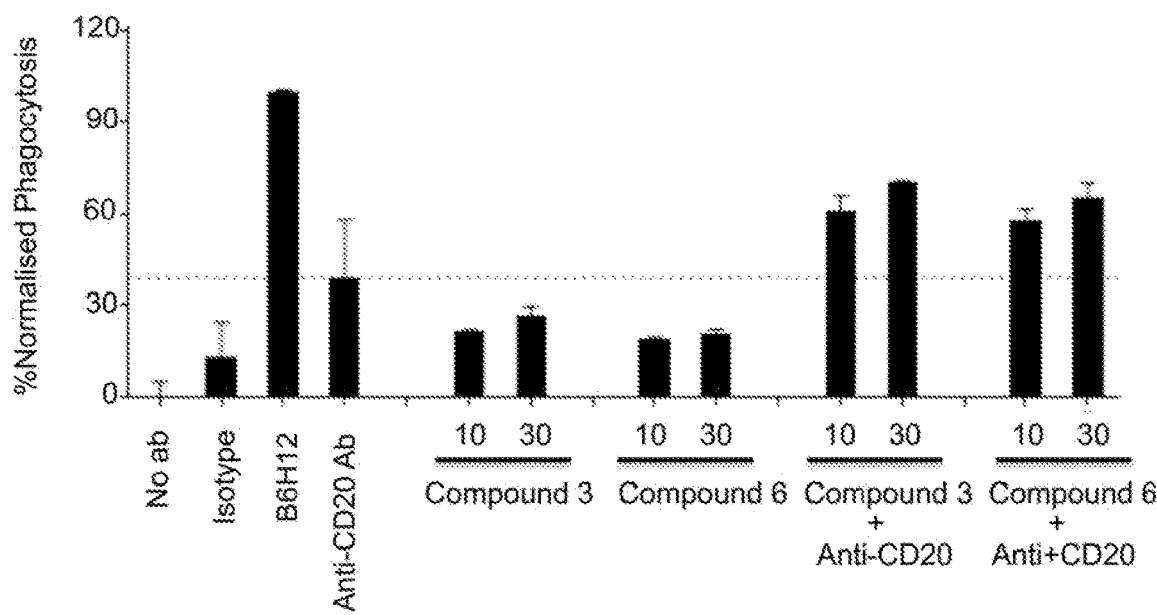
FIG. 1: Enhanced phagocytosis of lymphoma cells of Compound 3 and Compound 6 in combination with anti-CD20 antibody.

Each embodiment is provided by way of explanation of the invention, and not by way of limitation of the invention.

In fact, it will be apparent to those skilled in the art that various modifications and variations can be made to the compounds, compositions, and methods described herein without departing from the scope or spirit of the invention. For instance, features illustrated or described as part of one embodiment can be applied to another embodiment to yield a still further embodiment. Thus, it is intended that the present invention includes such modifications and variations and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In certain embodiments, the present invention provides a composition comprising CD47-SIRPα blocking agent and one or more anti-cancer agent(s), wherein the CD47-SIRPα blocking agent is represented by compound of formula (I):

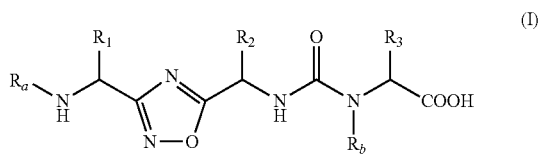

or a pharmaceutically acceptable salt or an amide or an ester, or a stereoisomer thereof; wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring;

$R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl, $R_b$ is hydrogen; and $R_3$ represents hydrogen, —CH$_2$-aryl, —$(CH_2)_3$NHC(=NH)NH$_2$, —$(CH_2)_2$CONH$_2$, —$(CH_2)_2$COOH, —$(CH_2)_4$NH$_2$ or —CH$_2$-heteroaryl, or $R_b$ and $R_3$, together with the atoms to which they are attached form a pyrrolidine ring.

In certain embodiments, the anti-cancer agent is a chemotherapeutic agent, or an immunomodulatory agent.

In certain embodiments, specific combination partners of interest for use with CD47-SIRPα blocking agents include therapeutic antibodies targeting tumor antigens that stimulate activating Fc receptors (FcRs) leading to efficient phagocytosis. In certain embodiments, specific combination partners of interest include therapeutic antibodies that stimulate Fc receptor-mediated phagocytosis. Hence antibodies selected from the group consisting of agents capable of triggering efficient phagocytosis include anti-CD20, e.g. rituximab, tiuxetan, tositumomab, etc., which combination finds particular use in the treatment of non-Hodgkin's B cell lymphomas and chronic lymphocytic leukemia (CLL). A combination with anti-CD22, e.g. Epratuzumab, etc. finds particular use in the treatment of B cell leukemia and hairy cell leukemia. A combination with anti-CD52, e.g. alemtuzumab, etc., finds particular use in the treatment of B cell and T cell leukemia, including without limitation chronic lymphocytic leukemia. A combination with anti-CD33, e.g. gemtuzumab ozogomicin, etc., finds particular use in the treatment of myeloid leukemia such as acute myelogenous leukemia. A combination with trastuzumab finds particular use in the treatment of breast cancer. A combination with bevacizumab finds particular use in the treatment of certain type of brain tumor, and certain types of cancers of the kidney, lung, colon, rectum, cervix, ovary, or fallopian tube. A combination with cetuximab finds particular use in the treatment of colon and head and neck cancer. A combination with panitumumab finds particular use in the treatment of colorectal cancer. A combination with daratumumab finds particular use in the treatment of multiple myeloma. Other combination of interest for treatment of myelogenous leukemias includes, without limitation, anti-CD96, anti-CD44 and anti-CD123.

In certain preferred embodiments, Fc receptors (FcRs) comprise Fc-gamma receptors (FcγR).

Other therapeutic antibodies that are of interest to combine with CD47-SIRPα blocking agents include but not limited to ofatumumab for chronic lymphocytic leukemia, obinutuzumab for follicular lymphoma, alemtuzumab for B-cell chronic lymphocytic leukaemia, Ibritumomab tiuxetan for B-cell non-Hodgkin lymphomas, dinutuximab for neuroblastoma and necitumumab for lung cancer.

In certain embodiments, the anticancer agent is anti-CD20 antibody such as rituximab, tiuxetan, tositumomab.

In certain embodiments, therapeutic agents known to activate prophagocytic receptors are also therefore ideal partners for use in combination with CD47-SIRPα blocking agents to achieve efficient phagocytosis. These agents include proteasome inhibitors (bortezomib, ixazomib and carfilzomib), Anthracyclines (Doxorubicin, Epirubicin, Daunorubicin, Idarubicin, Mitoxantrone) Oxaliplatin, Cyclophosphamide, Bleomycin, Vorinostat, Paclitaxel, 5-Fluorouracil, Cytarabine, BRAF inhibitory drugs (Dabrafenib, Vemurafenib), PI3K inhibitor, Docetaxel, Mitomycin C, Sorafenib, and Tamoxifen; or a combination thereof.

In certain embodiments, the anticancer agent is proteasome inhibitor.

In certain embodiments, the anticancer agent is bortezomib, ixazomib or carfilzomib or an analog thereof or a derivative thereof.

In certain embodiments, apart from the specific agents known to have effect on 'eat me' signals, other agents including Abiraterone acetate, Afatinib, Aldesleukin, Aldesleukin, Alemtuzumab, Anastrozole, Axitinib, Belinostat, Bendamustine, Bicalutamide, Blinatumomab, Bosutinib, Brentuximab, Busulfan, Cabazitaxel, Capecitabine, Carboplatin, Carfilzomib, Carmustine, Ceritinib, Clofarabine, Crizotinib, Dacarbazine, Dactinomycin, Dasatinib, Degarelix, Denileukin, Denosumab, Enzalutamide, Eribulin, Erlotinib, Everolimus, Exemestane, Exemestane, Fludarabine, Fulvestrant, Gefitinib, Goserelin, Ibritumomab, Imatinib, Ipilimumab, Irinotecan, Ixabepilone, Lapatinib, Lenalidomide, Letrozole, Leucovorin, Leuprolide, Lomustine, Mechlorethamine, Megestrol, Nelarabine, Nilotinib, Nivolumab, Olaparib, Omacetaxine, Palbociclib, Pamidronate, Panitumumab, Panobinostat, Pazopanib, Pegaspargase, Pembrolizumab, Pemetrexed Disodium, Pertuzumab, Plerixafor, Pomalidomide, Ponatinib, Pralatrexate, Procarbazine, Radium 223, Ramucirumab, Regorafenib, rIFNa-2b, Romidepsin, Sunitinib, Temozolomide, Temsirolimus, Thiotepa, Tositumomab, Trametinib, Vinorelbine, Methotrexate, Ibrutinib, Aflibercept, Toremifene, Vinblastine, Vincristine, Idelalisib, Mercaptopurine and Thalidomide could potentially have effect on 'eat me signal pathway on combining with CD-47-SIRPα blocking agents.

In yet other embodiments, in addition to the therapeutic agents mentioned above, other treatment modalities that are in use in cancer therapy also activate prophagocytic receptors, and thus can be combined with CD47-SIRPα blocking agents to achieve efficient phagocytosis. These include Hypericin-based photodynamic therapy (Hyp-PDT), radiotherapy, High-hydrostatic pressure, Photofrin-based PDT and Rose Bengal acetate-based PDT.

In certain embodiments, the chemotherapeutic agent is abarelix, aldesleukin, alitretinoin, allopurinol, altretamine, arsenic trioxide, asparaginase, azacitidine, bexarotene, baricitinib, bortezomib, busulfan intravenous, busulfan oral, calusterone, cetuximab, chlorambucil, cisplatin, cladribine, dalteparin sodium, decitabine, diftitox, disulfiram, dexrazoxane, dromostanolone propionate, eculizumab, estramustine, etoposide phosphate, etoposide, fentanyl citrate, filgrastim, floxuridine, gemcitabine, histrelin acetate, fosfamide, interferon alfa 2a, lapatinib ditosylate, levamisole, marizomib, meclorethamine, melphalan, mercaptopurine, methotrexate, methoxsalen, mitotane, nandrolone phenpropionate, nofetumomab, oprozomib, pegfilgrastim, pentostatin, pipobroman, plicamycin, procarbazine, quinacrine, rasburicase, ruxolitinib, rucaparib, streptozocin, teniposide, testolactone, thalidomide, thioguanine, topotecan, toremifene, tretinoin, uracil mustard, valrubicin, vinblastine, vincristine, niraparib, veliparib, talazoparib or zoledronate.

In certain embodiments, the anti-cancer agent is an immunomodulatory agent. In further embodiments, the immunomodulatory agent is costimulatory or coinhibitory molecule such as CTLA-4 (e.g., ipilimumab), 4-1BB (e.g., urelumab, and utomilumab), antibodies to PD-1 and PD-L1 (e.g., nivolumab, pembrolizumab, atezolizumab, Durvalumab and Camrelizumab), antibodies to cytokines (IL-10, TGF-.beta), antibodies to TIM-3, antibodies to LAG3, antibodies to B7H3, antibodies to B7H4 and antibodies to B7H6; or a combination thereof.

In some embodiments of the invention, two or more CD47-SIRPα blocking agents represented by compound of formula (I) are administered. In some embodiments, CD47-SIRPα blocking agents are administered more than once.

In certain embodiments, CD47-SIRPα blocking agent is an agent that blocks the interaction between CD47 and SIRPα. In certain embodiments, blocking the interaction between CD47 and SIRPα induces macrophage phagocytosis of tumor cells expressing CD47.

In certain embodiments, the present invention provides a composition comprising both small molecule CD47-SIRPα blocking agent as described in compound of formula (I), and a proteasome inhibitor. In certain embodiments, proteasome inhibitor is bortezomib, ixazomib or carfilzomib or any analogs thereof or derivative thereof.

In certain embodiments, the present composition includes a compound of formula (I), wherein $R_1$ is hydrogen, $—(CH_2)_2CONH_2$, $—(CH_2)_2COOH$, $—(CH_2)_3NHC(=NH)NH_2$, $—(CH_2)_4NH_2$, $—CH_2$-phenyl, or $—CH_2$-imidazolyl.

In certain embodiments, the present composition includes a compound of formula (I), wherein $R_1$ is $—(CH_2)_2CONH_2$, $—(CH_2)_2COOH$, $—(CH_2)_3NHC(=NH)NH_2$, or $—(CH_2)_4NH_2$.

In certain embodiments, the present composition includes a compound of formula (I), wherein $R_1$ is $—(CH_2)_2CONH_2$, or $—(CH_2)_2COOH$.

In certain embodiments, the present composition includes a compound of formula (I), wherein $R_2$ represents hydrogen, $—(CH_2)_3NHC(=NH)NH_2$, $—(CH_2)_2CONH_2$, $—(CH_2)_2COOH$, $—CH_2$-phenyl, or $—CH_2$-imidazolyl.

In certain embodiments, the present composition includes a compound of formula (I), wherein $R_2$ is hydrogen, $—(CH_2)_3NHC(=NH)NH_2$, or $—(CH_2)_2COOH$.

In certain embodiments, the present composition includes a compound of formula (I), wherein $R_2$ is hydrogen, $—(CH_2)_2CONH_2$, or $—(CH_2)_2COOH$.

In certain embodiments, the present composition includes a compound of formula (I), wherein $R_3$ represents hydrogen, $—CH_2$-phenyl, $—(CH_2)_3NHC(=NH)NH_2$, $—(CH_2)_2CONH_2$, $—(CH_2)_2COOH$, $—(CH_2)_4NH_2$ or $—CH_2$-imidazolyl.

In certain embodiments, the present composition includes a compound of formula (I), wherein $R_3$ represents hydrogen, $—CH_2$-phenyl, $—(CH_2)_3NHC(=NH)NH_2$, $—(CH_2)_2CONH_2$, $—(CH_2)_2COOH$, or $—(CH_2)_4NH_2$.

In certain embodiments, the present composition includes a compound of formula (I), wherein $R_a$ is hydrogen; and $R_1$ represents hydrogen, $—(CH_2)_2CONH_2$, $—(CH_2)_2COOH$, $—(CH_2)_3NHC(=NH)NH_2$, $—(CH_2)_4NH_2$, $—CH_2CONH_2$, $—CH_2$-phenyl, or $—CH_2$-imidazolyl, or $R_a$ and $R_1$, together with the atoms to which they are attached form a pyrrolidine ring;

$R_2$ represents hydrogen, $—(CH_2)_3NHC(=NH)NH_2$, $—(CH_2)_2CONH_2$, $(CH_2)_2COOH$, $—CH_2$-phenyl, or $—CH_2$-imidazolyl, $R_b$ is hydrogen; and $R_3$ represents hydrogen, $—CH_2$-phenyl, $—(CH_2)_3NHC(=NH)NH_2$, $—(CH_2)_2CONH_2$, $—(CH_2)_2COOH$, $—(CH_2)_4NH_2$ or $—CH_2$-imidazolyl, or $R_b$ and $R_3$, together with the atoms to which they are attached form a pyrrolidine ring.

In certain embodiments, the present composition includes a compound of formula (I) that is a compound of formula (IA):

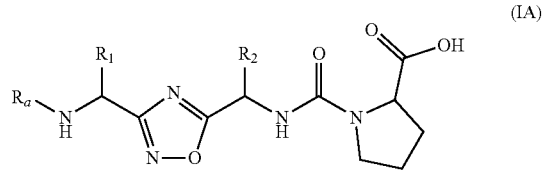

(IA)

or a pharmaceutically acceptable salt or an amide or an ester, or a stereoisomer thereof; wherein, $R_1$, $R_a$ and $R_2$ are as defined in compound of formula (I).

In certain embodiments, the present composition includes a compound of formula (IA), wherein $R_1$ represents hydrogen, $—(CH_2)_2CONH_2$, $—(CH_2)_2COOH$, $—(CH_2)_3NHC(=NH)NH_2$, $—(CH_2)_4NH_2$, $—CH_2$-phenyl, or $—CH_2$-imidazolyl.

In certain embodiments, the present composition includes a compound of formula (IA), wherein $R_2$ represents hydrogen, $—(CH_2)_3NHC(=NH)NH_2$, $—(CH_2)_2CONH_2$, $—(CH_2)_2COOH$, $—CH_2$-phenyl, or $—CH_2$-imidazolyl.

In certain embodiments, the present composition includes a compound of formula (IA), wherein $R_a$ is hydrogen; and $R_1$ represents hydrogen, $—(CH_2)_2CONH_2$, $—(CH_2)_2COOH$, $—(CH_2)_3NHC(=NH)NH_2$, $—(CH_2)_4NH_2$, $—CH_2$-phenyl, or $—CH_2$-imidazolyl, $R_2$ represents hydrogen, $—(CH_2)_3NHC(=NH)NH_2$, $—(CH_2)_2CONH_2$, $—(CH_2)_2COOH$, $—CH_2$-phenyl or $—CH_2$-imidazolyl.

In another embodiment, the present composition includes a compound of formula (IA), wherein $R_a$ is hydrogen; and $R_1$ represents $—(CH_2)_2CONH_2$, $—(CH_2)_2COOH$, $—(CH_2)_3NHC(=NH)NH_2$, or $—(CH_2)_4NH_2$. $R_2$ represents hydrogen, $—(CH_2)_3NHC(=NH)NH_2$, $—(CH_2)_2COOH$, $—CH_2$-phenyl or $—CH_2$-imidazolyl.

In certain embodiments, the present composition includes a compound of formula (I) selected from,

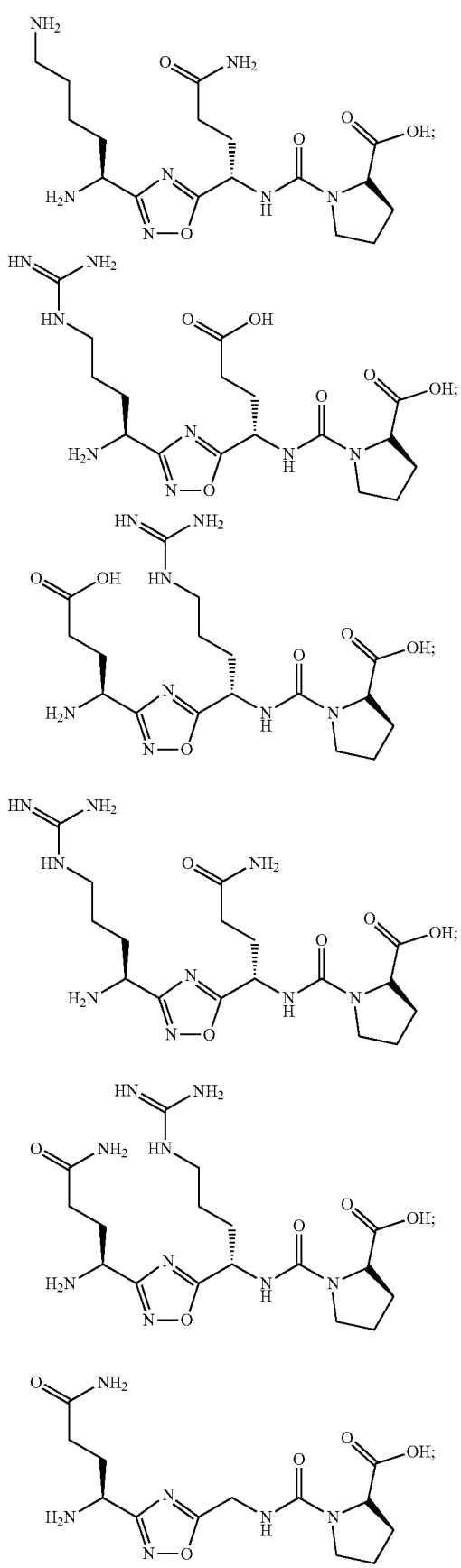
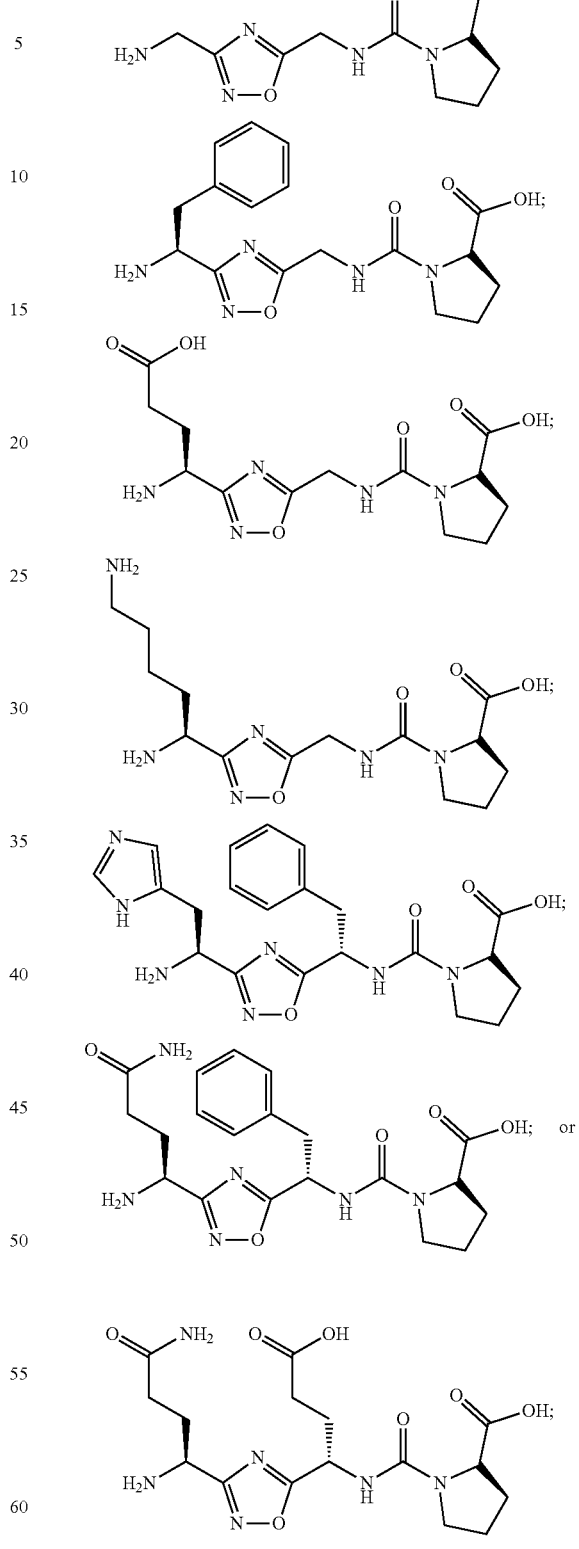
or a pharmaceutically acceptable salt or an amide or an ester, or a stereoisomer thereof.
In certain embodiments, the present composition includes a compound of formula (I) selected from,

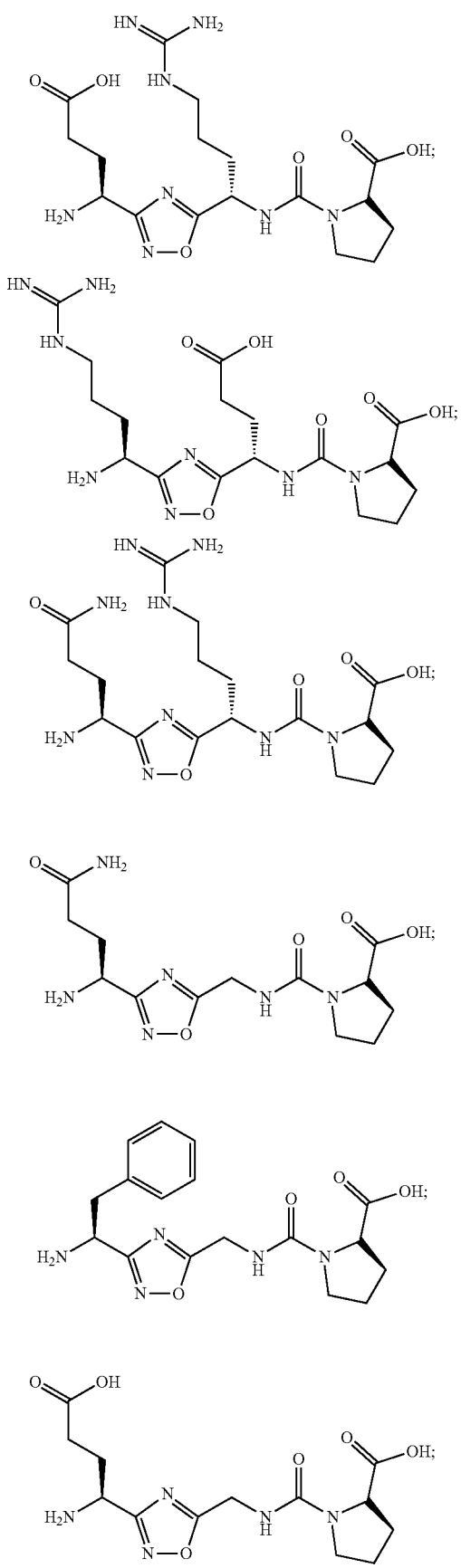

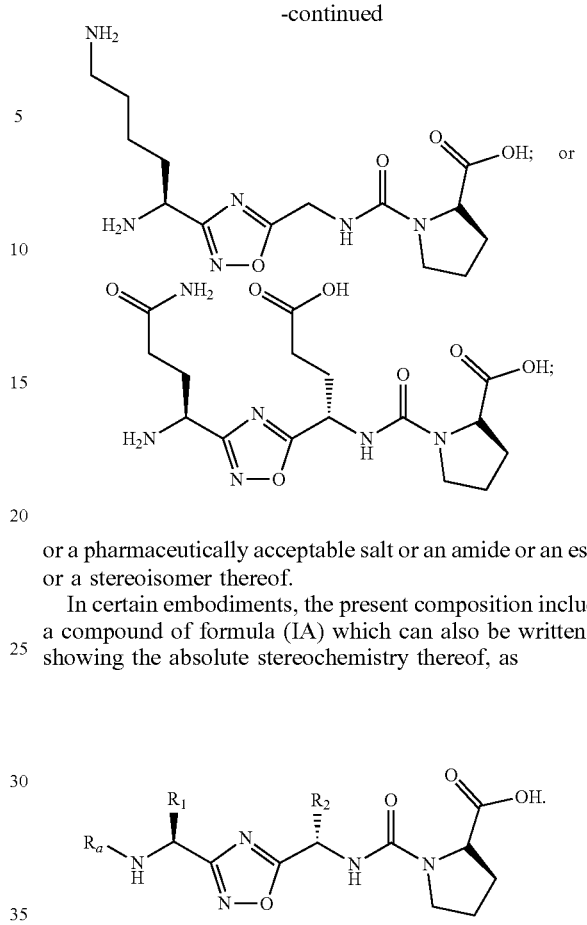

or a pharmaceutically acceptable salt or an amide or an ester, or a stereoisomer thereof.

In certain embodiments, the present composition includes a compound of formula (IA) which can also be written by showing the absolute stereochemistry thereof, as (IA)

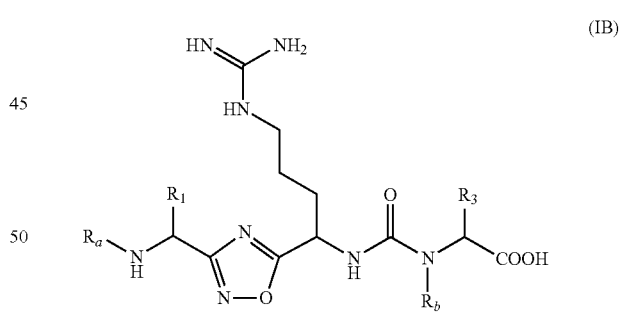

In certain embodiments, the present composition includes a compound of formula (I) that is a compound of formula (IB):

(IB)

or a pharmaceutically acceptable salt or an amide or an ester, or a stereoisomer thereof; wherein, $R_1$, $R_a$, $R_b$ and $R_3$ are as defined in compound of formula (I).

In certain embodiments, the present composition includes a compound wherein $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, or —$CH_2$-phenyl.

In certain embodiments, the present composition includes a compound wherein $R_1$ is —$(CH_2)_2$CONH$_2$, or —$(CH_2)_2$COOH.

In certain embodiments, the present composition includes a compound wherein $R_3$ is hydrogen, —$CH_2$-phenyl, —$(CH_2)_2$CONH$_2$, or —$(CH_2)_2$COOH.

In certain embodiments, the present composition includes a compound wherein R₃ is hydrogen, or —CH₂-phenyl.

In certain embodiments, the present composition includes a compound of formula (IB) wherein R_b is hydrogen.

In certain embodiments, in formula (IB), R_b and R₃, together with the atoms to which they are attached form a pyrrolidine ring.

In certain embodiments, the present composition includes a compound of formula (IB), wherein R₁ represents —(CH₂)₂CONH₂, or —(CH₂)₂COOH; R_b is hydrogen; and R₃ represents hydrogen, or —CH₂-phenyl, or R_b and R₃, together with the atoms to which they are attached form a pyrrolidine ring.

In certain embodiments, the present composition includes a compound of formula (I) wherein the compound is selected from,

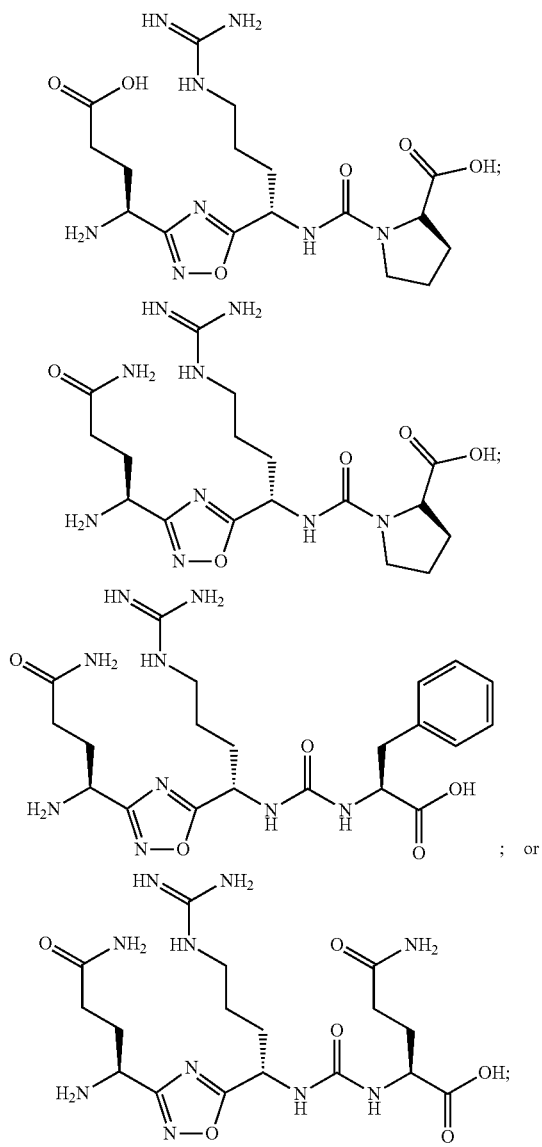

or a pharmaceutically acceptable salt or an amide or an ester, or a stereoisomer thereof.

In certain embodiments, the present composition includes a compound of formula (I) that is a compound of formula (IC):

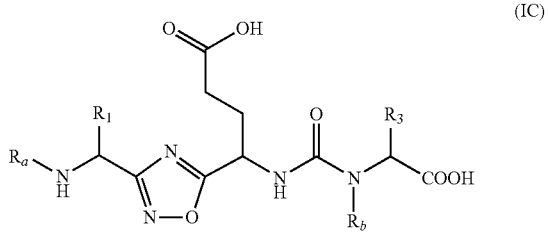

or a pharmaceutically acceptable salt or an amide or an ester, or a stereoisomer thereof; wherein, R₁, R_a, R₃ and R_b are as defined in compound of formula (I).

In certain embodiments, the present composition includes a compound wherein R₁ is —(CH₂)₂CONH₂, —(CH₂)₃NHC(=NH)NH₂, or —(CH₂)₄NH₂.

In certain embodiments, the present composition includes a compound wherein R₁ is —(CH₂)₂CONH₂, or —(CH₂)₃NHC(=NH)NH₂.

In certain embodiments, the present composition includes a compound of formula (IC), wherein R_a is hydrogen. In certain embodiments, in formula (IC), R_a and R₁, together with the atoms to which they are attached form a pyrrolidine ring.

In certain embodiments, the present composition includes a compound wherein R₃ is hydrogen, —CH₂-phenyl, —(CH₂)₃NHC(=NH)NH₂, or —CH₂-imidazolyl.

In certain embodiments, the present composition includes a compound of formula (IC), wherein R_b is hydrogen.

In certain embodiments, in formula (IC), R_b and R₃, together with the atoms to which they are attached form a pyrrolidine ring.

In another embodiment, the present composition includes a compound of formula (IC), wherein R_a is hydrogen; and R₁ represents —(CH₂)₂CONH₂, —(CH₂)₃NHC(=NH)NH₂, or —(CH₂)₄NH₂, or R_a and R₁, together with the atoms to which they are attached form a pyrrolidine ring; and R_b is hydrogen; and R₃ represents —CH₂-phenyl, —(CH₂)₃NHC(=NH)NH₂, or —CH₂-imidazolyl, or R_b and R₃, together with the atoms to which they are attached form a pyrrolidine ring.

In certain embodiments, the present composition includes a compound of formula (I), wherein the compound is selected from,

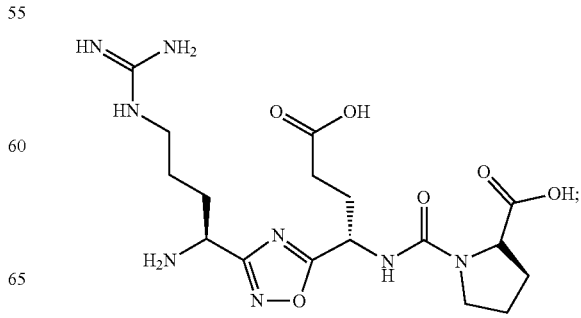

-continued

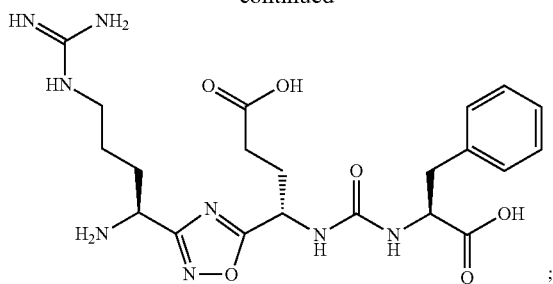

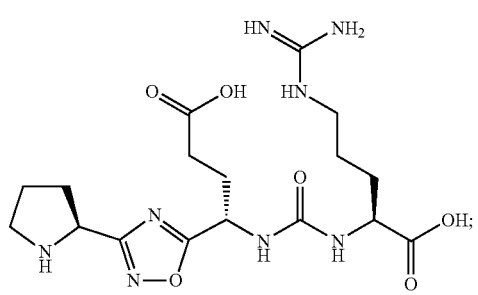

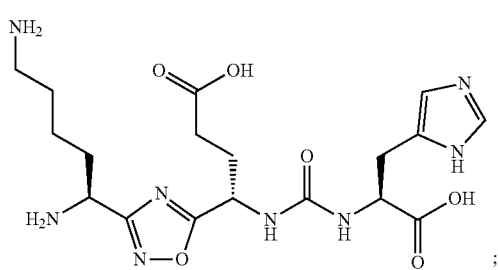

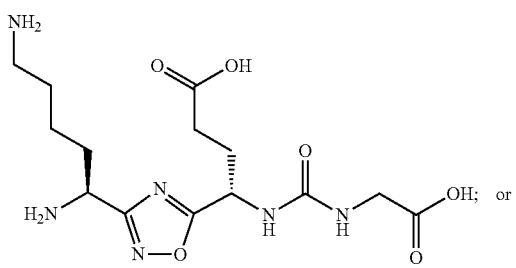

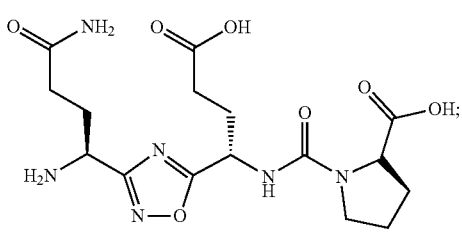

or a pharmaceutically acceptable salt or an amide or an ester, or a stereoisomer thereof.

In certain embodiments, the present composition includes a compound of formula (I) that is a compound of formula (ID):

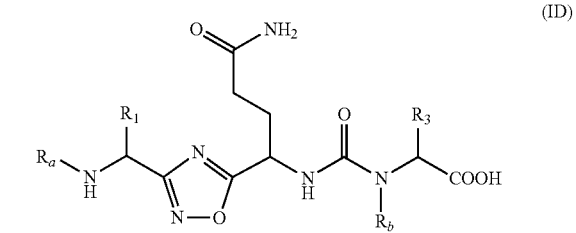

or a pharmaceutically acceptable salt or an amide or an ester, or a stereoisomer thereof; wherein, $R_1$, $R_a$, $R_3$ and $R_b$ are as defined in compound of formula (I).

In certain embodiments, the present composition includes a compound wherein, $R_1$ is —$(CH_2)_3NHC(=NH)NH_2$, —$(CH_2)_4NH_2$, or —$CH_2CONH_2$.

In certain embodiments, the present composition includes a compound wherein $R_3$ is hydrogen, —$(CH_2)_3NHC(=NH)NH_2$, or —$(CH_2)_4NH_2$.

In certain embodiments, the present composition includes a compound of formula (ID), wherein $R_b$ is hydrogen.

In certain embodiments, in formula (ID), $R_b$ and $R_3$, together with the atoms to which they are attached form a pyrrolidine ring.

In another embodiment, the present composition includes a compound of formula (ID), wherein $R_1$ represents —$(CH_2)_3$ NHC(=NH)NH_2, —$(CH_2)_4NH_2$, or —$CH_2CONH_2$, $R_b$ is hydrogen; and $R_3$ represents hydrogen, —$(CH_2)_3NHC(=NH)NH_2$, or —$(CH_2)_4NH_2$, or $R_b$ and $R_3$, together with the atoms to which they are attached form a pyrrolidine ring.

In certain embodiments, the present composition includes a compound of formula (I) wherein the compound is selected from,

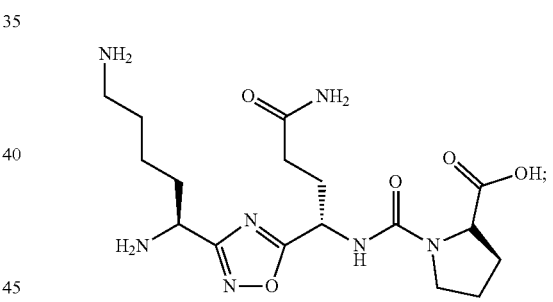

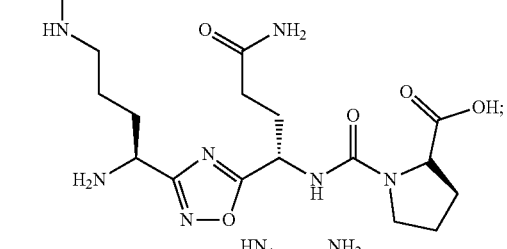

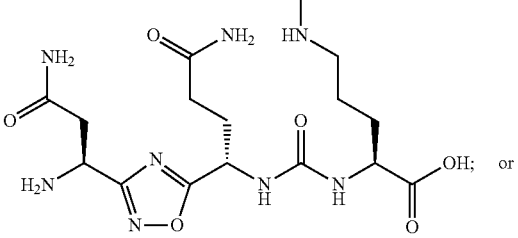

-continued

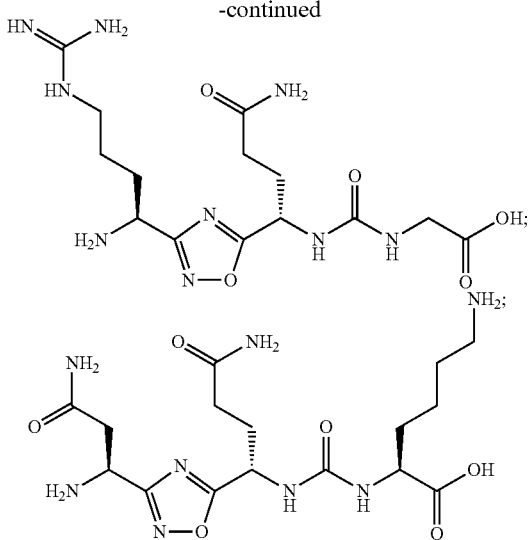

or a pharmaceutically acceptable salt or an amide or an ester, or a stereoisomer thereof. In certain embodiments, the present composition includes a compound of formula (I) that is a compound of formula (IE):

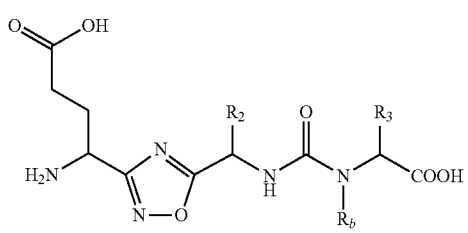

(IE)

or a pharmaceutically acceptable salt or an amide or an ester, or a stereoisomer thereof wherein, $R_2$, $R_3$ and $R_b$ are as defined in compound of formula (I).

In certain embodiments, the present composition includes a compound wherein $R_2$ is hydrogen, or —$(CH_2)_3$NHC(=NH)$NH_2$.

In certain embodiments, the present composition includes a compound of formula (IE), wherein $R_b$ and $R_3$, together with the atoms to which they are attached form a pyrrolidine ring.

In another embodiment, the present composition includes a compound of formula (IE), wherein, $R_2$ represents hydrogen, or —$(CH_2)_3$NHC(=NH)$NH_2$, $R_b$ and $R_3$, together with the atoms to which they are attached form a pyrrolidine ring.

In certain embodiments, the present composition includes a compound of formula (I) that is a compound of formula (IF):

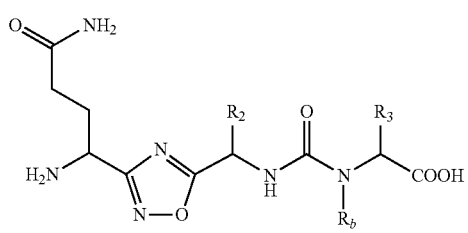

(IF)

or a pharmaceutically acceptable salt or an amide or an ester, or a stereoisomer thereof; wherein, $R_2$, $R_3$ and $R_b$ are as defined in compound of formula (I).

In certain embodiments, the present composition include a compound wherein $R_2$ is hydrogen, —$CH_2$-phenyl, —$(CH_2)_3$NHC(=NH)$NH_2$, or —$(CH_2)_2$COOH.

In certain embodiments, the present composition includes a compound wherein $R_3$ is —$CH_2$-phenyl, —$(CH_2)_2$CONH$_2$, or —$(CH_2)_2$COOH.

In certain embodiments, the present composition includes a compound of formula (IF), wherein $R_b$ is hydrogen.

In certain embodiments, in formula (IF), $R_b$ and $R_3$, together with the atoms to which they are attached form a pyrrolidine ring.

In certain embodiment, the present composition includes a compound of formula (IF), wherein $R_2$ represents hydrogen, —$CH_2$-phenyl, —$(CH_2)_3$NHC(=NH)$NH_2$, or —$(CH_2)_2$ COOH; $R_b$ is hydrogen; and $R_3$ represents —$CH_2$-phenyl, —$(CH_2)_2$CONH$_2$, or —$(CH_2)_2$COOH; or $R_b$ and $R_3$, together with the atoms to which they are attached form a pyrrolidine ring.

In certain embodiments, the present composition includes a compound of formula (I) wherein the compound is selected from:

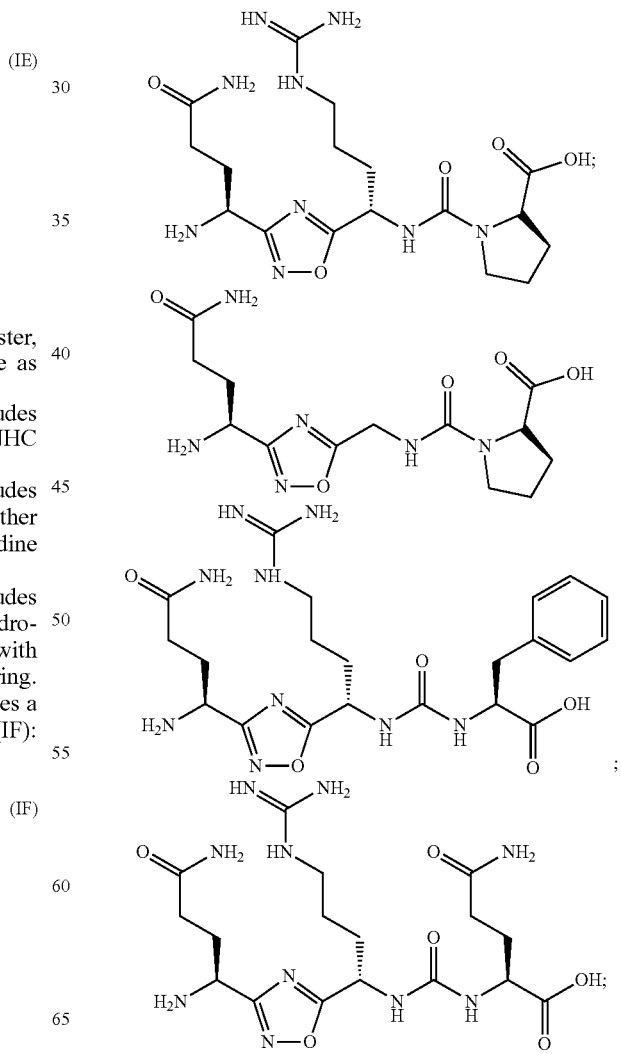

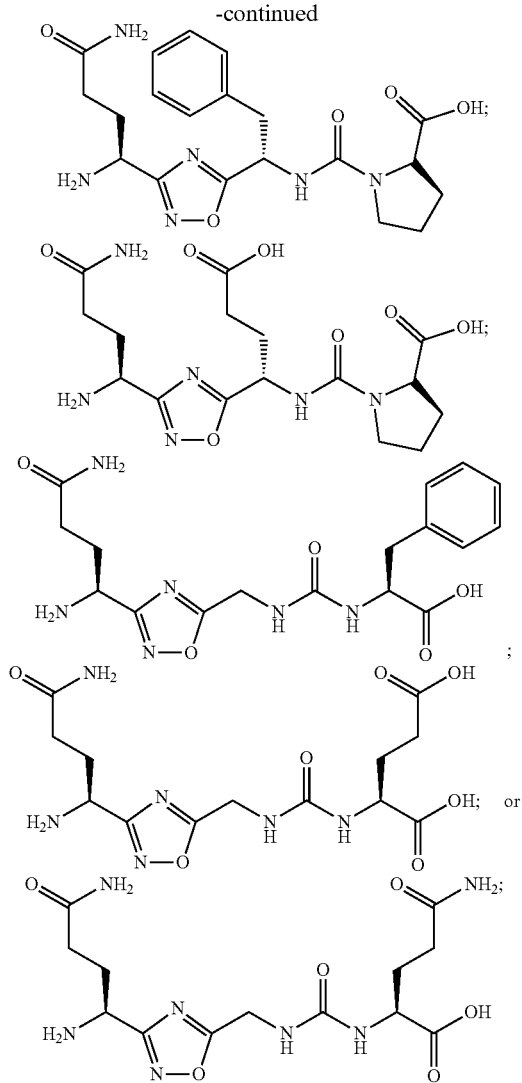
or a pharmaceutically acceptable salt or an amide or an ester, or a stereoisomer thereof.
In certain embodiments, the present composition includes a compound wherein the compound is selected from:

| Compound | Structure |
|---|---|
| 10 | 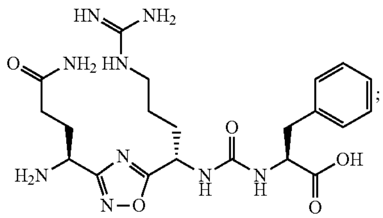 [SMILES: N=C(N)NCCC[C@H](NC(=O)N[C@@H](Cc1ccccc1)C(=O)O)c1nc([C@@H](N)CCC(N)=O)no1] |
| 11 | 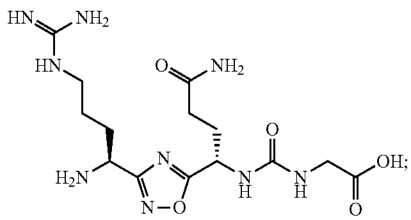 [SMILES: N=C(N)NCCC[C@H](N)c1noc([C@H](CCC(N)=O)NC(=O)NCC(=O)O)n1] |
| 12 | 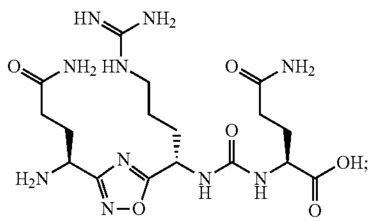 [SMILES: N=C(N)NCCC[C@H](NC(=O)N[C@@H](CCC(N)=O)C(=O)O)c1nc([C@@H](N)CCC(N)=O)no1] |
| 13 | 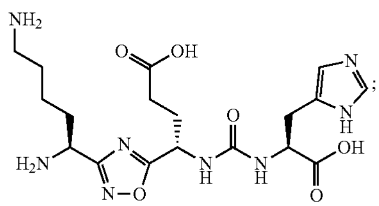 [SMILES: NCCCC[C@H](N)c1noc([C@H](CCC(=O)O)NC(=O)N[C@@H](Cc2cnc[nH]2)C(=O)O)n1] |
| 14 | 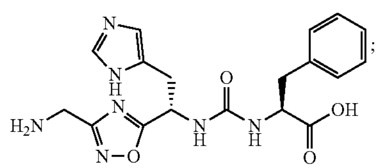 [SMILES: NCc1noc([C@H](Cc2cnc[nH]2)NC(=O)N[C@@H](Cc2ccccc2)C(=O)O)n1] |
| 15 | 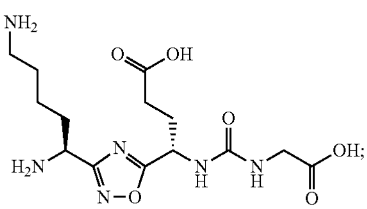 [SMILES: NCCCC[C@H](N)c1noc([C@H](CCC(=O)O)NC(=O)NCC(=O)O)n1] |
| 16 | 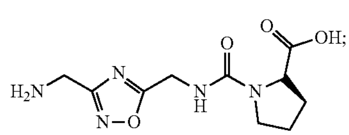 |
| 17 | 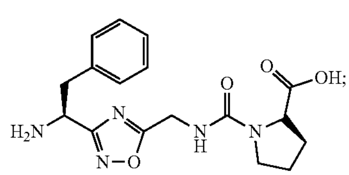 |

| Compound | Structure |
|---|---|
| 18 | 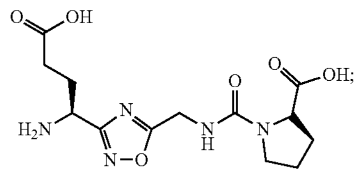 |
| 19 | 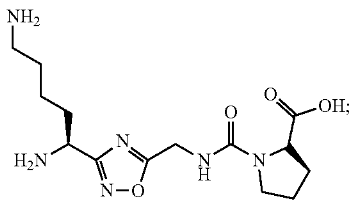 |
| 20 | 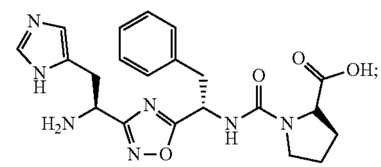 |
| 21 | 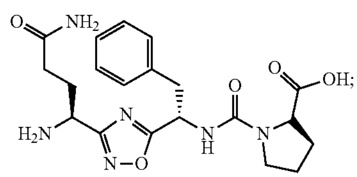 |
| 22 | 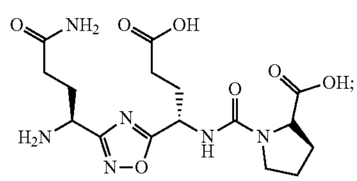 |
| 23 | 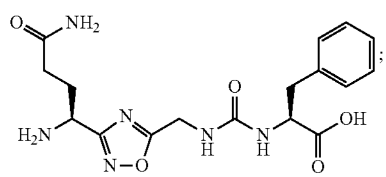 [SMILES: NC(=O)CC[C@H](N)c1noc(CNC(=O)N[C@@H](Cc2ccccc2)C(=O)O)n1] |
| 24 | 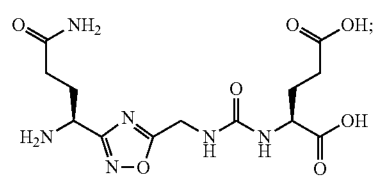 [SMILES: NC(=O)CC[C@H](N)c1noc(CNC(=O)N[C@@H](CCC(=O)O)C(=O)O)n1] |
| 25 | 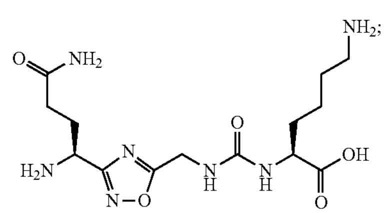 [SMILES: NCCCC[C@H](NC(=O)NCc1nc([C@@H](N)CCC(N)=O)no1)C(=O)O] |

| Compound | Structure |
|---|---|
| 26 | 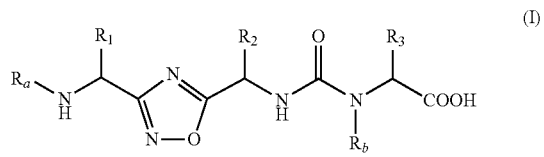 |
| 27 | | or a pharmaceutically acceptable salt or an amide or an ester, or a stereoisomer thereof.

In certain embodiments, the present invention relates to composition comprising CD47-SIRPα blocking agent and one or more anti-cancer agent(s) for use as a medicament wherein the CD47-SIRPα blocking agent is compounds of formula (I) or a pharmaceutically acceptable salt or an amide or an ester, or a stereoisomer thereof as described herein; and the anti-cancer agent is chemotherapeutic agent, or an immunomodulatory agent, as described herein.

In certain embodiments, the present invention relates to a composition comprising CD47-SIRPα blocking agent and one or more anti-cancer agent(s) and a pharmaceutically acceptable carrier, wherein the CD47-SIRPα blocking agent is compounds of formula (I) or a pharmaceutically acceptable salt or an amide or an ester, or a stereoisomer thereof as described herein; and the anti-cancer agent is chemotherapeutic agent, or an immunomodulatory agent, as described herein.

In certain embodiments, the present invention provides a combination comprising a CD47-SIRPα blocking agent and one or more anti-cancer agent(s), wherein the CD47-SIRPα blocking agent is represented by compound of formula (I):

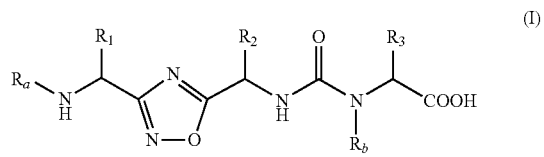

or a pharmaceutically acceptable salt or an amide or an ester, or a stereoisomer thereof; wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring;

$R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl, $R_b$ is hydrogen; and $R_3$ represents hydrogen, —CH$_2$-aryl, —$(CH_2)_3$NHC(=NH)NH$_2$, —$(CH_2)_2$CONH$_2$, —$(CH_2)_2$COOH, —$(CH_2)_4$NH$_2$ or —CH$_2$-heteroaryl, or $R_b$ and $R_3$, together with the atoms to which they are attached form a pyrrolidine ring.

In certain embodiments, the combination of present invention comprises the CD47-SIRPα blocking agent of compound of formula (I) and a proteasome inhibitor.

In certain embodiments, the combination of present invention comprises the CD47-SIRPα blocking agent of compound of formula (I) and an anti CD-20 antibody.

In certain embodiments, the combination of present invention comprises the CD47-SIRPα blocking agent of compound of formula (IA), (IB), (IC), (ID), (IE), or (IF).

In certain embodiments, the present invention relates to a method of treating cancer in a subject presenting a dysregulated CD47 pathway, the method comprising administering to the subject a therapeutically effective amount of CD47-SIRPα blocking agents in combination with a therapeutically effective amount of one or more anti-cancer agent(s), wherein the CD47-SIRPα blocking agents is represented by compound of formula (I):

$$\text{(I)}$$

or a pharmaceutically acceptable salt or an amide or an ester, or a stereoisomer thereof;

wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring; $R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl, $R_b$ is hydrogen; and $R_3$ represents hydrogen, —CH$_2$-aryl, —$(CH_2)_3$NHC(=NH)NH$_2$, —$(CH_2)_2$CONH$_2$, —$(CH_2)_2$COOH, —$(CH_2)_4$NH$_2$ or —CH$_2$-heteroaryl, or $R_b$ and $R_3$, together with the atoms to which they are attached form a pyrrolidine ring.

In certain embodiments, the subject presenting a dysregulated CD47 pathway is a subject presenting with CD47+ disease cells. In certain embodiments, CD47+ disease cells are CD47+ cancer cells.

In certain embodiments, the present invention relates to a method, wherein the treatment with one or more anti-cancer agent(s) is prior to, concomitant with, or following treatment with a compound of formula (I) or a pharmaceutically acceptable salt thereof.

In certain embodiments, the present invention relates to a method for treating or delaying progression of diseases or disorders mediated by CD47 pathway in a subject, the method comprising administering to the subject in need thereof a therapeutically effective amount of an agent blocking CD47-SIRPα pathway in combination with a therapeutically effective amount of one or more anti-cancer agent(s), wherein the agent blocking CD47-SIRPα pathway is represented by compound of formula (I):

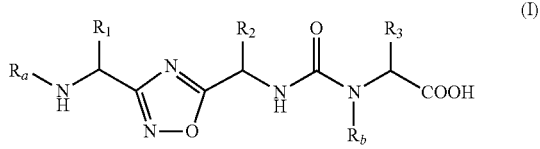

(I)

or a pharmaceutically acceptable salt or an amide or an ester, or a stereoisomer thereof;

wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl, or $R_a$ and $R_1$, together with the atoms to which they are attached form a pyrrolidine ring; $R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl, $R_b$ is hydrogen; and $R_3$ represents hydrogen, —CH$_2$-aryl, —$(CH_2)_3$NHC(=NH)NH$_2$, —$(CH_2)_2$CONH$_2$, —$(CH_2)_2$COOH, —$(CH_2)_4$NH$_2$ or —CH$_2$-heteroaryl, or $R_b$ and $R_3$, together with the atoms to which they are attached form a pyrrolidine ring.

In certain embodiments, the present invention relates to a method wherein the disease or disorder mediated by CD47-SIRPα pathway is cancer.

In certain embodiments, the present invention relates to a method wherein the disease or disorder mediated by CD47 pathway is atherosclerosis.

In certain embodiments, the present invention relates to a method wherein the disease or disorder mediated by CD47 pathway is multiple sclerosis.

In certain embodiments, the present invention provides a pharmaceutical composition comprising a compounds as disclosed herein, optionally admixed with a pharmaceutically acceptable carrier or diluent.

In certain embodiments, the present invention provides a use of a composition comprising CD47-SIRPα blocking agent and one or more anti-cancer agent(s) as described herein, in the manufacture of a medicament for the treatment of cancer in a subject presenting a dysregulated CD47 pathway.

In certain embodiments, the present invention provides a kit comprising a composition as described herein and a package insert comprising instructions for administration of the medicament to treat the subject presenting a dysregulated CD47 pathway.

The present invention also provides methods for formulating the disclosed compounds for pharmaceutical administration.

The compositions and methods of the present invention may be utilized to treat an individual in need thereof. In certain embodiments, the individual is a mammal such as a human, or a non-human mammal. When administered to an animal, such as a human, the composition is preferably administered as a pharmaceutical composition comprising, for example, compound of the invention and a pharmaceutically acceptable carrier. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The agents in the composition are administered concomitantly, i.e. each agent is administered within about 45 days, 30 days, 15 days, 7 days, 3 days, 2 days, 1 day or substantially simultaneously with respect to the other agent(s) in the combination. The agents can be considered to be combined if administration scheduling is such that the serum level of both agents is at a therapeutic level.

In certain embodiments, for administration, each the dose of CD47-SIRPα blocking agent and the anticancer agent(s), in combination, will be within the range from about 0.0001 to 100 mg/kg, and more usually 0.01 to 50 mg/kg, of the host body weight. For example dosages can be 1 mg/kg body weight, 10 mg/kg body weight or 30 mg/kg body weight, or within the range of 1-50 mg/kg. The dosage may be adjusted for the molecular weight of the CD47-SIRPα blocking agent or an anticancer agent as described and may be reduced relative to the dosage required for a monotherapy of either agent in the combination. An exemplary treatment regime entails administration daily, semi-weekly, weekly, once every two weeks, once a month, etc.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water.

The formulations may conveniently be presented in unit dosage form and may be prepared by any methods well known in the art of pharmacy. The amount of each active ingredient in the composition which can be combined with a carrier material to produce a single dosage form will vary depending upon the host being treated, the particular mode of administration. The amount of each active ingredient in the composition that can be combined with a carrier material to produce a single dosage form will generally be that amount of the compound that produces a therapeutic effect. Generally, out of one hundred percent, this amount will range from about 1 percent to about ninety-nine percent of each active ingredient, preferably from about 5 percent to about 70 percent, most preferably from about 10 percent to about 30 percent.

Methods of preparing these formulations or compositions include the step of bringing into association the present composition with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a composition of the present invention as an therapeutically active combination. Compositions may also be administered as a bolus, electuary or paste.

To prepare solid dosage forms for oral administration (capsules (including sprinkle capsules and gelatin capsules), tablets, pills, dragees, powders, granules and the like), the composition as described is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the combined active ingredients therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredients can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredients, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredients, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active ingredients of the present composition with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredients.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants.

The active compounds may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compounds of the present composition at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

In general, a suitable daily dose of an active compound used in the compositions and methods of the invention will be that amount of the compound that is the lowest dose effective to produce a therapeutic effect. Such an effective dose will generally depend upon the factors described above.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the composition described herein enhance macrophage phagocytic activity towards a cancer cell, e.g., an AML cell. In other embodiments, the phagocytic activity is enhanced, e.g., 1%, 5%, 10%, 20%, 30%, 40%, 50%, 60%, 70%, 80%, or 90%, relative to a macrophage in the absence of the composition described herein.

In certain embodiments, the present invention provides uses of composition of the present invention for the preparation of a medicament.

In certain embodiments, the present invention provides uses of composition of the present invention for the preparation of a medicament, e.g., for the treatment of cancer.

In certain embodiments, the present invention provides methods for treating cancer, wherein the method comprises administration of composition of the present invention, e.g., in a therapeutically effective amount, to the subject in need thereof.

In certain embodiments, the present invention provides methods for inhibiting growth of tumour cells and/or metastasis by administering a composition of the present invention, e.g., in a therapeutically effective amount, to the subject in need thereof.

Representative tumour cells include cells of a cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, acute lymphocytic leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), non-small cell lung cancer (NSCLC), primary CNS lymphoma, tumour angiogenesis, spinal axis tumour, brain stem glioma, pituitary adenoma, Kaposi's sarcoma, epidermoid cancer, squamous cell cancer, T-cell lymphoma, B-cell lymphomas, myeloproliferative disorder/neoplasm (MPDS); myelodysplastic syndrome; giant cell myeloma, heavy-chain myeloma, light chain myeloma and Bence-Jones myeloma, environmentally induced cancers including those induced by asbestos (e.g., mesothelioma), and combinations of said cancers. The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term 'compound(s)' comprises the compounds of formula (I), (IA), (IB), (IC), (ID), (IE), (IF) and their pharmaceutically acceptable salts or stereoisomers thereof.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls and/or heterocyclyls. Aryl groups include benzene, naphthalene, phenanthrene, and the like. Preferably the term 'aryl' includes phenyl.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls and/or heterocyclyls. Heteroaryl groups include, for example, pyrrole, furan, thiophene, imidazole, oxazole, thiazole, pyrazole, pyridine, pyrazine, pyridazine, indole, 1,2,4-oxadiazole, 1,3,4-oxadiazole, 1,3,4-thiadiazole, benzimidazole, pyrimidine and the like. A heteroaryl group may be substituted at one or more positions, as permitted by valence, with any optional substituents described herein. Preferably the term 'heteroaryl' includes imidazolyl, and indolyl.

As used herein, a therapeutic that "prevents" a disorder or condition refers to a compound that, in a statistical sample, reduces the occurrence of the disorder or condition in the treated sample relative to an untreated control sample or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate or stabilize the existing unwanted condition or side effects thereof).

As used herein, the phrase "delaying progression" refers to the procedures or applications that are intended to delay in time the development of a disease or symptoms of a disease (including delaying in time the appearance or occurrence of at least one symptom of the particular disease).

The term "prodrug" is intended to encompass compounds which, under physiologic conditions, are converted into the therapeutically active agents of the present invention (e.g., a compound of formula (I)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula (I) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

As used herein, the term "including" as well as other forms, such as "include", "includes," and "included," is not limiting.

As used herein, the term "disease" or "disorder" refers to a pathological condition in an organism resulting from cause or condition including, but not limited to, infections, acquired conditions, genetic conditions, and characterized by identifiable symptoms.

As used herein, "patient" or "subject" or "individual" to be treated includes humans and or non-human animals, including mammals. Mammals include primates, such as humans, chimpanzees, gorillas and monkeys; domesticated animals, such as dogs, horses, cats, pigs, goats, cows; and rodents such as mice, rats, hamsters and gerbils.

The term CD47+ disease cells means cells having the phenotype CD47+ and are associated with a disease. In one embodiment, the CD47+ disease cells are cancer cells.

The term "CD47+" is used with reference to the phenotype of cells targeted for binding by the present CD47-SIRPα blocking agent. Cells that are CD47+ can be identified by flow cytometry using CD47 antibody as the affinity ligand. CD47 antibodies that are labeled appropriately are available commercially for this use (for example, the antibody product of clone B6H12 is available from Santa Cruz Biotechnology). The cells examined for CD47 phenotype can include standard tumour biopsy samples including particularly blood samples taken from the subject suspected of harboring endogenous CD47+ cancer cells. CD47 disease cells of particular interest as targets for therapy with the present drug combinations are those that "over-express" CD47. These CD47+ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry or by immunostaining or by gene expression analysis or the like, to be greater than the level measurable on a healthy counterpart cell having a CD47 phenotype that is normal for that cell type.

This invention includes the compositions comprising pharmaceutically acceptable salts of compounds described herein and their use in the compositions and methods of the present invention. In certain embodiments, contemplated salts include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

As used herein, the term "pharmaceutically acceptable salt" is intended to include all salts known and used in the art of pharmaceuticals. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Exemplary pharmaceutically acceptable salts include acetate, lactobionate, benzenesulfonate, laurate, benzoate, malate, bicarbonate, maleate, bisulfate, mandelate, bitartrate, mesylate, borate, methylbromide, methylnitrate, calcium edetate, methylsulfate, camsylate, mucate, carbonate, napsylate, bromide, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate and valerate, which can be used as a dosage form for modifying the solubility or hydrolysis characteristics or can be used in sustained release or prodrug formulations. The preparation of the pharmaceutically acceptable salts described above and other typical pharmaceutically acceptable salts is more fully described by Berg et al., "Pharmaceutical Salts," J. Pharm. Sci. 66: 1-19 (1977).

The term "stereoisomers" refers to any enantiomers, diastereoisomers, or geometrical isomers, such as of the compounds described herein. When such compounds are chiral, they can exist in racemic or in optically active form. Since the pharmaceutical activity of the racemates or stereoisomers of the compounds according to the invention may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

The term "ester", as used herein, refers to a group —C(O)OR$_{11}$ wherein R$_{11}$ represents a hydrocarbyl group.

The term "amide", as used herein, refers to a group —C(O)NH$_2$.

In certain embodiments, compounds described in this invention may be racemic. In certain embodiments, compounds described in this invention may be enriched in one enantiomer. For example, a compound described in this invention may have greater than 30% ee, 40% ee, 50% ee, 60% ee, 70% ee, 80% ee, 90% ee or even 95% or greater ee. In certain embodiments, compounds described in this invention may have more than one stereocenter. In certain such embodiments, compounds described in this invention may be enriched in one or more diastereomer. For example, a compound described in this invention may have greater than 30% de, 40% de, 50% de, 60% de, 70% de, 80% de, 90% de or even 95% or greater de.

The term "subject" includes mammals (especially humans) and other animals, such as domestic animals (e.g., household pets including cats and dogs) and non-domestic animals (such as wildlife).

In certain embodiments, the present invention provides a composition comprising of small molecule CD-47-SIRPα pathway inhibitors with agents capable of activating receptors such as Fc-receptors (FcRs) or prophagocytic receptors or other treatment modalities that are in use in cancer therapy to activate prophagocytic receptors for exploiting the maximum potential of the CD-47-SIRPα pathway blockade.

Example-1

The synthetic procedure for the preparation of compounds described in the present invention were described in co-pending Indian provisional patent application 201841001438 dated 12 Jan. 2018, which is converted as PCT application PCT/IB2019/050219, the contents of which are hereby incorporated by reference in their entirety.

Biological Example:
Reagents

DPBS (Gibco), RPMI 1640 WITH HEPES AND L-GLN-500 ML (Lonza), Recombinant Human M-CSF(R& D systems), CD47 Monoclonal Antibody (B6H12), Functional Grade antibody (Ebioscience), Mouse IgG1 kappa Isotype Control, Functional Grade (Ebioscience), Vacutainer (multiple sample luer adapter) (BD), Vacutainer (sodium heparin (NH) 158USP units, Blood collection tubes (BD), Histopaque (density-1.077 gm/ml) (SIGMA 1077), Trypan Blue solution (SIGMA-T8154), Hemacytometer (Bright line-SIGMA Z359629), Scalp vein infusion set (JMS), Cell Dissociation buffer (Gibco), 48 well sterile flat bottom plates (Corning), Luciferase expressing Raji cells (Generated in house by trasfection of luciferase gene in Raji cells) Luminometer, Hygromycin B (Invitrogen), Bright Glo luciferase assay system (Promega), 96 well plate, polystyrene, high band, white flat bottom wells (Sigma CLS3912), Anti-human CD20 antibody (Invivogen hcd20-mab1), Bortezomib (Selleckchem, S1013)

Example-2: Luciferase Based Phagocytosis Assay

In vitro phagocytosis assay was performed to evaluate the ability of test item to enhance the phagocytic activity of macrophages. Monocytes were isolated from blood of healthy donor and cultured for 6-8 days using 10% RPMI (Roswell Park Memorial Institute) media and recombinant human M-CSF to differentiate into macrophages. Media was changed every alternate day. After differentiation, adherent macrophages were collected by gentle scraping and cultured in 10% RPMI overnight at a density of 0.1 million per well in 48 well tissue culture plate. Simultaneously, luciferase expressing Raji (lymphoma cell line) cells were cultured in 10% RPMI media with 100 µg/mL of hygromycin B in tissue culture flask. On the day of phagocytosis, macrophages were serum starved for 2 hours. 0.4 million luciferase expressing Raji cells per well were incubated with anti-human CD47 antibody or Mouse IgG1 K Isotype Control antibody or various concentrations of selected compounds of the present invention alone or in combination with anti-human CD20 antibody in serum free media for 30 min at 37° C. and added into respective well of the 48 well plate seeded with macrophages. After 2 hours, cells were washed twice with PBS and 100 µl of serum free RPMI was added to each well. Additionally, 50 µl bright glow reagent was added to each well followed by mixing of cells and incubated for 5 min in dark. Luminescence reading was taken using plate reader after transferring the content of each well to white plate. Intensity of luminescence indicated the extent of phagocytosis. Each experimental condition was carried out in duplicate. The results are given in FIG. 1.

Results in FIG. 1 shows that the treatment of tumor cells with anti-human CD20 antibody leads to a significant increase in phagocytosis as compared to CD47-SIRPα blockade compound alone.

Example-3: Human Macrophage Phagocytosis Assay to Evaluate Compounds in Combination with Bortezomib In vitro phagocytosis assay was performed to evaluate the ability of test item to enhance the phagocytic activity of macrophages. Monocytes were isolated from blood of healthy donors and cultured for 6-8 days using complete RPMI (Roswell Park Memorial Institute) supplemented with 20 ng/mL recombinant human M-CSF to differentiate them into macrophages. Media was changed every alternate day. Simultaneously H929 cells were cultured in complete RPMI media and treated with 10 nM bortezomib for 48 hrs. Macrophages were starved for 2 hrs in serum free RPMI.CFSE stained, Bortezomib treated/untreated H929 (multiple myeloma cell line) cells were seeded at a density of $0.2 \times 10^6$ cells/well in 96-well low attachment plate and treated with anti-human CD47 purified B6H12 (5 µg/mL)/ Mouse IgG1 K Isotype Control antibody (5 µg/mL)/different concentrations of selected compounds of the present invention in serum free media for 30 min at 37° C. Serum starved macrophages were added to H929 cells at a ratio of 1:4 (macrophages:H929 cells) and incubated for 2 hours at 37° C. Cells in each well were stained with anti-human CD11b APC for 30 minutes at 4° C. in dark followed by fixation and FACS analysis. Cells positive for FITC and APC were considered as H929 cells phagocytosed by macrophages. Data acquired using FACS verse was analysed using Flow Jo software. The results are given in FIG. 2.

Figure 2:
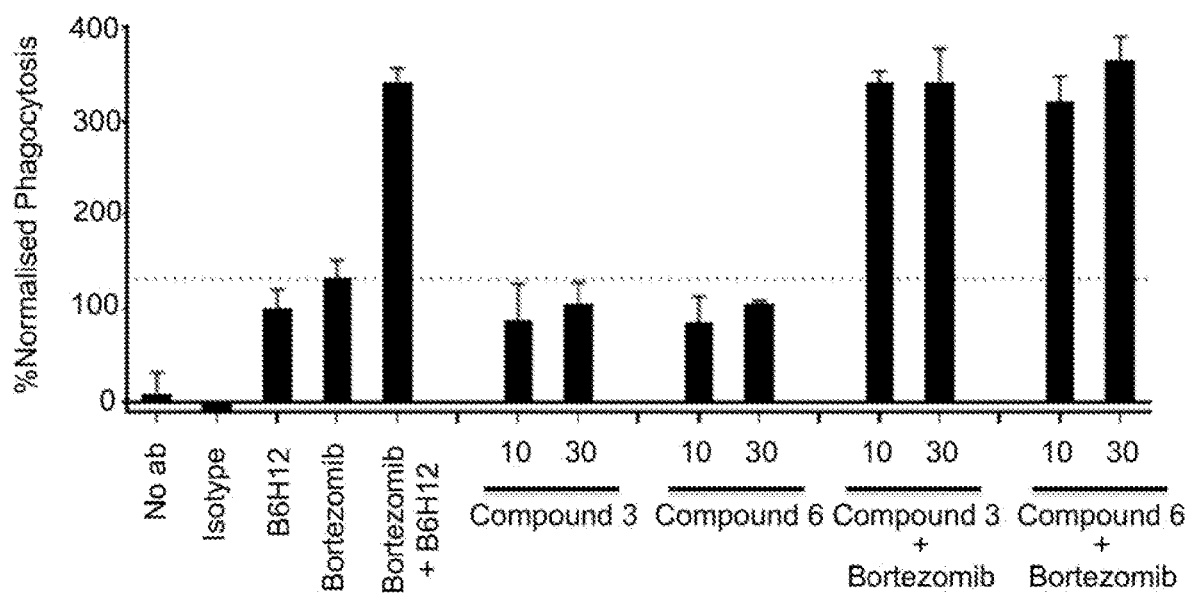
FIG. 2: Enhanced phagocytosis of multiple myeloma cells of Compound 3 and Compound 6 in combination with bortezomib.

Results in FIG. 2 shows that the treatment of tumor cells with proteasome inhibitors (bortezomib) leads to a significant increase in phagocytosis as compared to CD47-SIRPα blockade compound alone.

Example-4: Efficacy Study of Compound 6 in Combination with PD-L1 Antibody in A20 Syngeneic Lymphoma Model Female Balb/c (BALB/cAnNTac) mice (6-8 weeks-old) bred in-house were used in this efficacy study in the A20 syngeneic lymphoma model. The animals were marked individually with tail marks and kept in cages that were identified by a cage card showing the study code, date of experimentation, sex and number of animals. During the experiment, the animals were weighed daily. A20 cell line (B-cell lymphoma line derived from a spontaneous reticulum cell neoplasm found in an old BALB/cAnN mouse) was procured from ATCC.

When the mean tumor volumes reached approximately 75 mm$^3$, the animals were randomized based on tumor volumes into four groups (G1 to G4) of twelve animals (N=12) each and dosed with vehicle, Compound 6, anti-mouse PD-L1 antibody and the combination of Compound 6 and anti-mouse PD-L1 antibody as mentioned below:

| Group | Compound | Dose | Frequency | Route | Dose volume |
|---|---|---|---|---|---|
| G1 | Vehicle control | 0 mg/kg | Twice daily (bid) | Oral | 10 mL/kg |
| G2 | Compound 6 | 30 mg/kg | Twice daily (bid) | Oral | 10 mL/kg |
| G3 | Anti-mouse PD-L1 antibody (Clone 10F.9G2) | 200 µg/animal | On Day 1, Day 3, Day 6 and Day 9 | i.p | 100 µL/mouse |
| G4 | Compound 6 + Anti-mouse PD-L1 antibody (Clone 10F.9G2) | 30 mg/kg + 200 µg/animal | Twice daily (bid) + On Day 1, Day 3, Day 6 and Day 9 | Oral, i.p | 10 mL/kg, 100 µL/mouse |

The treatment was continued for a period of 21 days, during which the overall efficacy and tolerability were evaluated based on tumor volume and body weight changes observed during the treatment period.

Individual animal body weights were recorded daily before the administration of Compound 6 throughout the experimental period. Animals were observed for mortality/morbidity once daily throughout the experimental period and were also observed for clinical signs once daily throughout the experimental period. The tumor volumes were measured in all treatment group animals thrice a week (once every 2-3 days) using a digital Vernier callipers. From an ethical viewpoint, any treatment/control group with a mean tumor weight in excess of 10% of animal body weight were humanely sacrificed. As a measure of efficacy, the % T (treatment)/C(control) and % TGI (% Tumor growth inhibition) values were calculated. Graphs and statistical analysis were performed using GraphPad Prism®, Version 7.0. For analysis of tumor volume data, statistical comparison was done on Day 18 for all groups using One-way ANOVA with Dunnett's multiple comparison test. All analyses and comparisons was evaluated at the 5% (p<0.05) level. A "p" value less than 0.05 was considered as significant. The results and statistics are summarised in the table given below:

| Group | Compound | Dose | % TGI |
|---|---|---|---|
| 1 | Vehicle control | 0 mg/kg (bid) | — |
| 2 | Compound 6 | 30 mg/kg (bid) | 72* |
| 3 | Anti-mouse PD-L1 Antibody | 200 µg/animal | 41 |
| 4 | Compound 6 + Anti-mouse PD-L1 antibody | 30 mg/kg (bid) + 200 µg/animal | 90*** |

Figure 3:
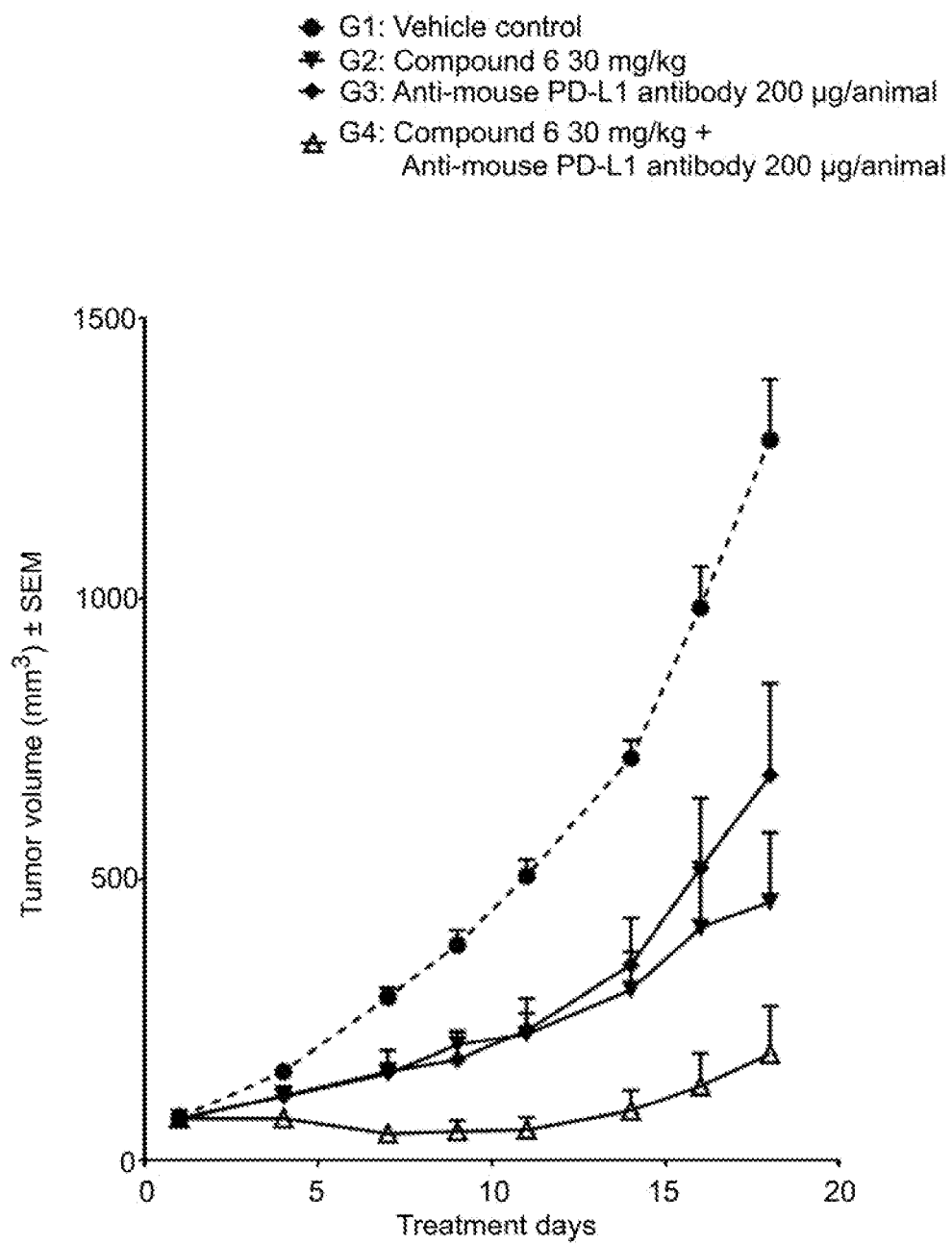
FIG. 3: Anti-tumor efficacy of Compound 6 alone and in combination with anti-mouse PD-L1 antibody in A20 tumor bearing mice.

One-way ANOVA, Dunnett's multiple comparison's test: *-p<0.05, ***-p<0.001, TGI—tumor growth inhibition;

Compound 6 at 30 mg/kg bid dose, both as single agent as well as in combination with PD-L1 antibody, was well tolerated without any treatment related clinical signs and mortality indicating excellent tolerability of the tested agents at the dosage administered. At the end of treatment period, Compound 6 dosed at 30 mg/kg alone, anti-mouse PD-L1 antibody alone and Compound 6 in combination with anti-mouse PD-L1 antibody showed tumor growth inhibition (TGI) values of 72%, 41% and 90%, respectively. Effect of treatments on tumor growth kinetics are graphically represented in FIG. 3.

It was further observed that Compound 6 when combined with anti-mouse PD-L1 antibody resulted in significantly enhanced tumor growth inhibition along with more a durable response when compared to individual treatments. 5 out of 11 animals treated with combination treatment of Compound 6 and anti-mouse PD-L1 antibody showed complete tumor regression. Tumor growth inhibition observed with Compound 6 individual treatment and combination treatment of compound 6 with anti-mouse PD-L1 antibody were statistically significant.

We claim:

1. A combination comprising a CD47-SIRPα blocking agent and one or more anti-cancer agent(s), wherein the CD47-SIRPα blocking agent is represented by a compound of formula (I):

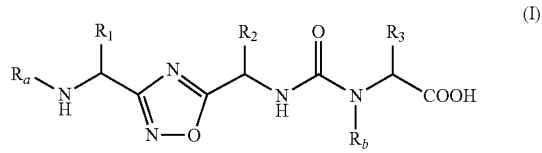

or a pharmaceutically acceptable salt thereof or an amide thereof or an ester thereof, or a stereoisomer thereof; wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl; or $R_a$ and $R_1$, together with the atoms to which they are attached form a pyrrolidine ring;

$R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl;

$R_b$ and $R_3$, together with the atoms to which they are attached form a pyrrolidine ring.

2. The combination of claim 1, wherein the anti-cancer agent is a chemotherapeutic agent or an immunomodulatory agent.

3. The combination of claim 2, wherein the chemotherapeutic agent is a proteasome inhibitor (bortezomib, ixazomib and carfilzomib), Anthracyclines (Doxorubicin, Epirubicin, Daunorubicin, Idarubicin, Mitoxantrone), Oxaliplatin, Cyclophosphamide, Bleomycin, Vorinostat, Paclitaxel, 5-Fluorouracil, Cytarabine, BRAF inhibitory drugs (Dabrafenib, Vemurafenib), a PI3K inhibitor, Docetaxel, Mitomycin C, Sorafenib, or Tamoxifen, or a combination thereof.

4. The combination of claim 2, wherein the chemotherapeutic agent is Abiraterone acetate, Afatinib, Aldesleukin, Alemtuzumab, Anastrozole, Axitinib, Belinostat, Bendamustine, Bicalutamide, Blinatumomab, Bosutinib, Brentuximab, Busulfan, Cabazitaxel, Capecitabine, Carboplatin, Carfilzomib, Carmustine, Ceritinib, Clofarabine, Crizotinib, Dacarbazine, Dactinomycin, Dasatinib, Degarelix, Denileukin, Denosumab, Enzalutamide, Eribulin, Erlotinib, Everolimus, Exemestane, Exemestane, Fludarabine, Fulvestrant, Gefitinib, Goserelin, Ibritumomab, Imatinib, Ipilimumab, Irinotecan, Ixabepilone, Lapatinib, Lenalidomide, Letrozole, Leucovorin, Leuprolide, Lomustine, Mechlorethamine, Megestrol, Nelarabine, Nilotinib, Nivolumab, Olaparib, Omacetaxine, Palbociclib, Pamidronate, Panitumumab, Panobinostat, Pazopanib, Pegaspargase, Pembrolizumab, Pemetrexed Disodium, Pertuzumab, Plerixafor, Pomalidomide, Ponatinib, Pralatrexate, Procarbazine, Radium 223, Ramucirumab, Regorafenib, rIFNa-2b, Romidepsin, Sunitinib, Temozolomide, Temsirolimus, Thiotepa, Tositumomab, Trametinib, Vinorelbine abarelix, aldesleukin, alitretinoin, allopurinol, altretamine, arsenic trioxide, asparaginase, azacitidine, bexarotene, baricitinib, bortezomib, busulfan intravenous, busulfan oral, calusterone, cetuximab, chlorambucil, cisplatin, cladribine, dalteparin sodium, decitabine, diftitox, disulfiram, dexrazoxane, dromostanolone propionate, eculizumab, estramustine, etoposide phosphate, etoposide, fentanyl citrate, filgrastim, floxuridine, gemcitabine, histrelin acetate, fosfamide, interferon alfa 2a, lapatinib ditosylate, levamisole, marizomib, meclorethamine, melphalan, mercaptopurine, methotrexate, methoxsalen, mitotane, nandrolone phenpropionate, nofetumomab, oprozomib, pegfilgrastim, pentostatin, pipobroman, plicamycin, procarbazine, quinacrine, rasburicase, ruxolitinib, rucaparib, streptozocin, teniposide, testolactone, thalidomide, thioguanine, topotecan, toremifene, tretinoin, uracil mustard, valrubicin, vinblastine, vincristine, niraparib, veliparib, talazoparib, zoledronate, Ibrutinib, Aflibercept, or Idelalisib.

5. The combination of claim 2, wherein the immunomodulatory agent is a costimulatory molecule or a coinhibitory molecule comprising CTLA-4 (e.g., ipilimumab), 4-1BB (e.g., urelumab, and utomilumab), antibodies to PD-1 and PD-L1 (e.g., nivolumab, pembrolizumab, atezolizumab, Durvalumab and Camrelizumab), antibodies to cytokines (IL-10, TGF-.beta.), antibodies to TIM-3, antibodies to LAG3, antibodies to B7H3, antibodies to B7H4, or antibodies to B7H6, or a combination thereof.

6. The combination of claim 1, wherein the anticancer agent is a therapeutic antibody targeting tumor antigens that stimulate activating Fc receptors (FcRs).

7. The combination of claim 6, wherein the therapeutic antibody is selected from the group capable of triggering efficient phagocytosis comprising anti-CD20 (rituximab, tiuxetan, tositumomab), which combination finds particular use in the treatment of non-Hodgkin's B cell lymphomas and chronic lymphocytic leukemia (CLL); anti-CD22, (Epratuzumab) which combination finds particular use in the treatment of B cell leukemia and hairy cell leukemia; anti-CD52, (alemtuzumab) which combination finds particular use in the treatment of B cell and T cell leukemia, (chronic lymphocytic leukemia); anti-CD33 (gemtuzumab ozogomicin) which combination finds particular use in the treatment of myeloid leukemia (acute myelogenous leukemia); trastuzumab which combination finds particular use in the treatment of breast cancer; bevacizumab which combination finds particular use in the treatment of certain type of brain tumor, and certain types of cancers of kidney, lung, colon, rectum, cervix, ovary, or fallopian tube; cetuximab which combination finds particular use in the treatment of colon and head and neck cancer; panitumumab which combination finds particular use in the treatment of colorectal cancer; anti-CD38 (daratumumab) which combination finds particular use in the treatment of multiple myeloma; CD96, anti-CD44, anti-CD123 which combination finds particular use in the treatment of myelogenous leukemias; ofatumumab which combination finds particular use in the treatment of chronic lymphocytic leukemia; obinutuzumab which combination finds particular use in the treatment of follicular lymphoma; alemtuzumab which combination finds particular use in the treatment of B-cell chronic lymphocytic leukaemia; Ibritumomab tiuxetan which combination finds particular use in the treatment of B-cell non-Hodgkin lymphomas; dinutuximab which combination finds particular use in the treatment of neuroblastoma; and necitumumab which combination finds particular use in the treatment of lung cancer.

8. The combination of claim 1, wherein $R_1$ represents hydrogen, —$(CH_2)_2CONH_2$, —$(CH_2)_2COOH$, —$(CH_2)_3NHC(=NH)NH_2$, —$(CH_2)_4NH_2$, —$CH_2CONH_2$, —$CH_2$-phenyl, or —$CH_2$-imidazolyl.

9. The combination of claim 1, wherein $R_2$ represents hydrogen, —$(CH_2)_3NHC(=NH)NH_2$, —$(CH_2)_2CONH_2$, —$(CH_2)_2COOH$, —$CH_2$-phenyl, or —$CH_2$-imidazolyl.

10. The combination of claim 1, wherein the CD47-SIRPα blocking agent is represented by a compound of formula (IA)

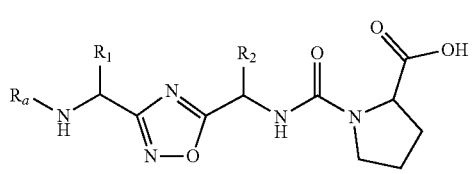

(IA)

or a pharmaceutically acceptable salt or an amide or an ester, or a stereoisomer thereof; wherein, $R_1$, $R_a$ and $R_2$ are as defined in claim 1.

11. The combination of claim 10, wherein $R_1$ represents hydrogen, —$(CH_2)_2CONH_2$, —$(CH_2)_2COOH$, —$(CH_2)_3NHC(=NH)NH_2$, —$(CH_2)_4NH_2$, —$CH_2$-phenyl, or —$CH_2$-imidazolyl.

12. The combination of claim 10, wherein $R_2$ represents hydrogen, —$(CH_2)_3NHC(=NH)NH_2$, —$(CH_2)_2CONH_2$, —$(CH_2)_2COOH$, —$CH_2$-phenyl, or —$CH_2$-imidazolyl.

13. The combination of claim 1, wherein the CD47-SIRPα blocking agent is represented by a compound of formula (IB)

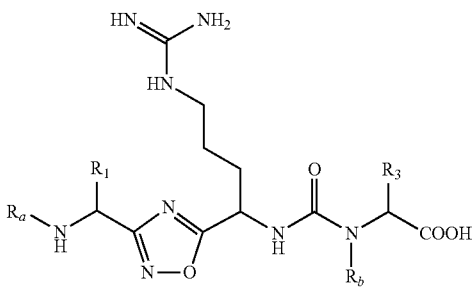

(IB)

or a pharmaceutically acceptable salt or an amide or an ester, or a stereoisomer thereof.

14. The combination of claim 13, wherein $R_1$ represents hydrogen, —$(CH_2)_2CONH_2$, —$(CH_2)_2COOH$, —$(CH_2)_3NHC(=NH)NH_2$, —$(CH_2)_4NH_2$, or —$CH_2$-phenyl.

15. The combination of claim 13, wherein $R_b$ and $R_3$, together with the atoms to which they are attached form a pyrrolidine ring.

16. The combination of claim 1, wherein the CD47-SIRPα blocking agent is selected from the group consisting of:

| Compound | Structure |
|---|---|
| 1 | ![structure 1] |
| 2 | ![structure 2] |
| 3 | ![structure 3] |
| 4 | ![structure 4] |
| 5 | ![structure 5] |
| 6 | ![structure 6] |

-continued

| Compound | Structure |
|---|---|
| 16 | 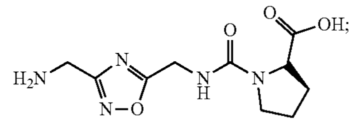 |
| 17 | 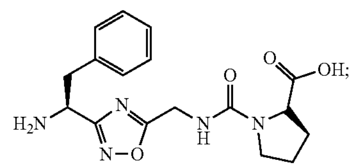 |
| 18 | 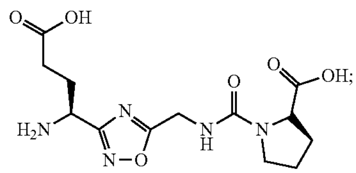 |
| 19 | 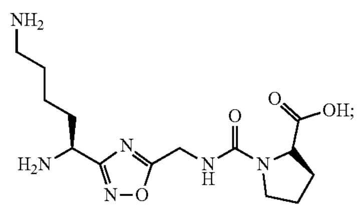 |
| 20 | 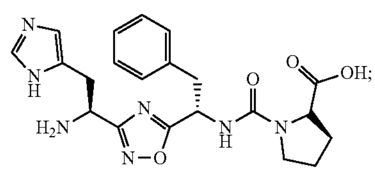 |
| 21 | 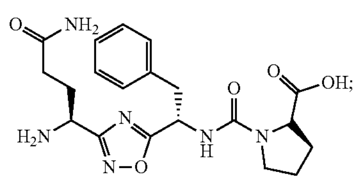 |
| 22 | | or a pharmaceutically acceptable salt or an amide or an ester, or a stereoisomer thereof.

17. A pharmaceutical composition comprising the combination of a CD47-SIRPα blocking agent and one or more anti-cancer agent(s) as claimed in claim 1, and a pharmaceutically acceptable carrier.

18. A method for treating or delaying progression of diseases or disorders mediated by dysregulated CD47-SIRPα pathway in a subject, the method comprising administering to the subject in need thereof a therapeutically effective amount of an agent blocking CD47-SIRPα pathway in combination with a therapeutically effective amount of one or more anti-cancer agent(s), wherein the agent blocking CD47-SIRPα pathway is represented by compound of formula (I):

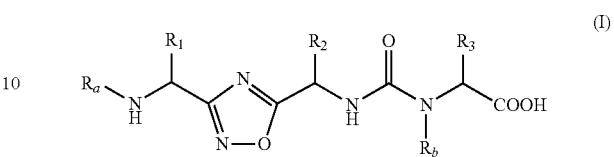

(I)

or a pharmaceutically acceptable salt or an amide or an ester, or a stereoisomer thereof; wherein, $R_a$ is hydrogen; and $R_1$ represents hydrogen, —$(CH_2)_2$CONH$_2$, —$(CH_2)_2$COOH, —$(CH_2)_3$NHC(=NH)NH$_2$, —$(CH_2)_4$NH$_2$, —CH$_2$CONH$_2$, —CH$_2$-aryl, or —CH$_2$-heteroaryl; or $R_a$ and $R_1$, together with the atoms to which they are attached form a pyrrolidine ring;

$R_2$ represents hydrogen, —$(CH_2)_3$NHC(=NH)NH$_2$, —$(CH_2)_2$CONH$_2$, —$(CH_2)_2$COOH, —CH$_2$-aryl, or —CH$_2$-heteroaryl;

$R_b$ and $R_3$, together with the atoms to which they are attached form a pyrrolidine ring.

19. The method of claim 18, wherein the subject presenting a dysregulated CD47-SIRPα pathway is a subject presenting with CD47+ disease cells.

20. The method of claim 18, wherein the disease or disorder mediated by dysregulated CD47-SIRPα pathway is a cancer.

21. The method of claim 20, wherein the cancer is selected from the group consisting of melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, acute lymphocytic leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), non-small cell lung cancer (NSCLC), primary CNS lymphoma, tumour angiogenesis, spinal axis tumour, brain stem glioma, pituitary adenoma, Kaposi's sarcoma, epidermoid cancer, squamous cell cancer, T-cell lymphoma, B-cell lymphomas, myeloproliferative disorder/neoplasm (MPDS); myelodysplastic syndrome; giant cell myeloma, heavy-chain myeloma, light chain myeloma and Bence-Jones myeloma, environmentally induced cancers including those induced by asbestos (e.g., mesothelioma), and combinations of said cancers.

* * * * *